(12) United States Patent
Gomez et al.

(10) Patent No.: US 11,969,507 B2
(45) Date of Patent: Apr. 30, 2024

(54) APPARATUS AND PROCESS FOR PRODUCING NANOCARRIERS AND/OR NANOFORMULATIONS

(71) Applicant: Evonik Operations GmbH, Essen (DE)

(72) Inventors: Mario Gomez, Darmstadt (DE); Jürgen Erwin Lang, Karlsruhe (DE); Marcel Arndt, Moerfelden-Walldorf (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/550,409

(22) PCT Filed: Mar. 8, 2022

(86) PCT No.: PCT/EP2022/055859
§ 371 (c)(1),
(2) Date: Sep. 13, 2023

(87) PCT Pub. No.: WO2022/194615
PCT Pub. Date: Sep. 22, 2022

(65) Prior Publication Data
US 2024/0091166 A1   Mar. 21, 2024

(30) Foreign Application Priority Data

Mar. 17, 2021   (EP) .................................... 21163221

(51) Int. Cl.
*B01F 25/27*   (2022.01)
*A61K 9/51*   (2006.01)
*B01J 13/08*   (2006.01)

(52) U.S. Cl.
CPC .......... *A61K 9/5192* (2013.01); *A61K 9/5123* (2013.01); *B01F 25/27* (2022.01); *B01J 13/08* (2013.01)

(58) Field of Classification Search
CPC ....................................................... B01F 25/27
(Continued)

(56) References Cited

U.S. PATENT DOCUMENTS 3,847,375 A * 11/1974 Kuerten ................ B01F 25/211
366/101
4,511,535 A * 4/1985 Schmidt ................... B01J 19/20
366/322
(Continued)

FOREIGN PATENT DOCUMENTS

WO   02/094222   11/2002
WO   2004/002453   1/2004
(Continued)

OTHER PUBLICATIONS

Extended European Search Report dated Sep. 3, 2021, in European Patent Application No. 21163221.1, 6 pages.
(Continued)

*Primary Examiner* — David L Sorkin
(74) *Attorney, Agent, or Firm* — Grüneberg and Myers PLLC

(57) ABSTRACT

An apparatus and corresponding process can be used for producing nanocarriers and or nanoformulations and corresponding process products. The apparatus is characterized by a vertical orientation of the feed conduits leading to active element. The feed conduits are nested within one another and are axially movable in terms of their orientation to one another. The process provides for the mixing of at (Continued)

least two liquid phases with different acidities. The volume flow of the first phase is greater than that of the second phase.

22 Claims, 10 Drawing Sheets

(58) Field of Classification Search
USPC .............................. 366/167.1, 173.1, 178.1
See application file for complete search history.

(56) References Cited

U.S. PATENT DOCUMENTS

| | | | | |
|---|---|---|---|---|
| 4,999,131 | A * | 3/1991 | Shimizu | B01F 23/41 |
| | | | | 516/53 |
| 7,434,982 | B2 * | 10/2008 | Nagasawa | B01F 25/3132 |
| | | | | 366/147 |
| 7,579,191 | B2 * | 8/2009 | Nagasawa | B01F 25/3132 |
| | | | | 422/652 |
| 8,187,554 | B2 * | 5/2012 | Panagiotou | B01F 33/30 |
| | | | | 366/162.4 |
| 2001/0050881 | A1 * | 12/2001 | Depaoli | B01F 33/3032 |
| | | | | 204/554 |
| 2003/0190563 | A1 * | 10/2003 | Nagasawa | B01F 31/86 |
| | | | | 430/569 |
| 2004/0180005 | A1 | 9/2004 | Jurgens et al. | |
| 2023/0138197 | A1 | 5/2023 | Torres et al. | |

FOREIGN PATENT DOCUMENTS

| | | |
|---|---|---|
| WO | 2007/012191 | 2/2007 |
| WO | 2011/127255 | 10/2011 |
| WO | 2015/048020 | 4/2015 |
| WO | 2017/223135 | 12/2017 |
| WO | 2019/136241 | 7/2019 |

OTHER PUBLICATIONS

International Search Report dated Jun. 24, 2022, in PCT/EP2022/055859, 7 pages.
Written Opinion dated Jun. 24, 2022, in PCT/EP2022/055859, 7 pages.
U.S. Appl. No. 17/918,849, filed Oct. 13, 2022, Torres et al.

* cited by examiner

APPARATUS AND PROCESS FOR PRODUCING NANOCARRIERS AND/OR NANOFORMULATIONS

CROSS-REFERENCE TO RELATED APPLICATIONS

This application is the National Stage entry under § 371 of International Application No. PCT/EP2022/055859, filed on Mar. 8, 2022, and which claims the benefit of priority to European Application No. 21163221.1, filed on Mar. 17, 2021. The content of each of these applications is hereby incorporated by reference in its entirety.

BACKGROUND OF THE INVENTION

Field of the Invention

In the context of the present invention a nanocarrier is a composition for carrying pharmaceutical, cosmetic or nutraceutical active ingredients. The nanocarrier may consist of a pure substance or may be a mixture of two or more substances. The substances may be solid, semi-fluid or liquid. The substances may be single-phase or multi-phase substances: In all cases nanocarriers are in particulate form, wherein the average particle size is smaller than 300 nm.

Description of Related Art

Examples of nanocarriers are particles of natural or synthetic polymers, lipids (lipid nanoparticles—LNP), liposomes and micelles and nanoemulsions.

Nanocarriers composed of two or more substances are generally produced by providing the individual substances or precursors thereof as dispersions or as solutions in liquid media and mixing these with one another. The mixing results in physical interactions between the individual substances or precursors to form the nanocarrier. The nanocarrier may optionally be subjected to subsequent workup, for example by separation from the liquid medium. The obtained nanocarrier may then either be used as a placebo or is laden with an active ingredient to form a nanoformulation.

In the context of the present invention a nanoformulation is a dosage form of a pharmaceutical, cosmetic or nutraceutical active ingredient carried by a nanocarrier. The active ingredient may be on the surface of the nanocarrier, may be inside the nanocarrier or may be complexed with the nanocarrier.

Examples of nanoformulations include inter alia so-called lipoplexes or polyplexes, i.e. complexes of polymers or lipids with for example DNA, RNA, proteins, peptides etc. Within these complexes the polymers/lipids form the nanocarrier while the DNA/RNA form the active ingredient.

As described above the production of nanoformulations may be carried out by loading a nanocarrier with active ingredient.

However, in pharmaceutical technology it is in the interest of process economy that the production of the nanocarrier and the loading thereof with active ingredient is carried out in an integrated process:

In such an integrated process the nanocarrier is produced first and loaded with active ingredient in the nascent state. This is generally carried out by providing and mixing the individual components of the nanoformulation as a dispersion or solution in liquid media. The components include the substances forming the nanocarrier/precursors to these substances and also the active ingredient or its precursors. The mixing results in physical interactions between the individual components to form the nanoformulation. If required, the nanoformulation is subsequently subjected to further workup, for instance separated from the liquid medium.

Especially nanoformulations using LNP or polyplexes as the carrier are always produced in an integrated process where the loading of the carrier with active ingredient is carried out in the nascent state.

An essential apparatus engineering aspect in the production of nanocarriers/nanoformulations is the design of the mixers with which the components dispersed or dissolved in the liquid media are mixed.

In conventional mixers the problem is the mixing itself. The mixers are therefore made small, so-called micromixers. In such a micromixer the mass flow is divided into many small substreams and the substreams are mixed. These small structures are very sensitive to fouling (deposits on the wall) and small gas bubbles. The reactants for micromixers must therefore be conditioned for high-purity conditions. This means that especially dissolved gases such as air or nitrogen must be laboriously removed from the liquid.

EP1519714B1 discloses a process for producing nanoformulations employing an apparatus comprising a T-shaped mixer. The two fluids to be mixed are passed through coaxial feed conduits to a collision point, mixed there and withdrawn through a discharge offset by 90°. The angle between the two feed conduits is 180°. The volume flow of the two fluids into the active element is the same.

EP1937213B1 discloses a process and an apparatus for producing nanoformulations where two T-shaped mixers are arranged in series. Thus, three fluids may be mixed in two steps. The disadvantage of this constellation is that T-shaped mixers form flow conditions which change upon increasing the production scale—so-called scaling up (fluid-mechanical similarity problem). The altered flow conditions bring about altered production properties. For this reason it is non-trivial to transfer the operating conditions optimized in terms of product quality in laboratory and pilot operation to a larger production scale. Instead, industrial operation comprises simultaneously operating a multiplicity of small-scale apparatuses with the conditions optimized on the pilot scale ("numbering up"). This increases capital costs. A further disadvantage of this process is that the production of LNP forms a mixture, in whose milieu the nanocarriers are not stable for long. Consequently the nanocarriers must either be separated from the mixture particularly quickly or stabilized in an additional step. Both options make process management very laborious.

EP3711749A1 discloses Y-shaped mixers for producing nanoformulations. The two feed conduits to the collision point are thus not parallel. The Y-mixer may be combined with a T-mixer to produce triphasic mixtures. Y-mixers likewise have complex flow dynamics and can therefore be transferred from pilot scale to production scale only through "numbering up". The problem of inadequate stability of LNP in the obtained mixture is also encountered in processes with Y-mixers.

WO2001005373A1 discloses a mixing head for producing nanoformulations comprising a plurality of injectors having a diameter of less than 2 mm.

WO2017223135A1 discloses a mixing head which likewise operates according to the injector principle. The injector is provided with a metering apparatus which is in the form of a servomotor-actuated pipette.

SUMMARY OF THE INVENTION

The present invention has for its object to specify an apparatus for producing nanocarriers/nanoformulations, whose fluid-mechanical ratios are retained even in the course of a scale up, so that increasing production scale is possible without "numbering up".

Furthermore, the process for producing nanocarriers/nanoformulations operated with the apparatus shall save operating steps.

The object is achieved by an apparatus and by a process performable using this apparatus as described below.

The present invention thus provides an apparatus for producing nanocarriers and/or nanoformulations which has the following features:

a first reservoir vessel for accommodating a first liquid phase;
a second reservoir vessel for accommodating a second liquid phase;
an active element for providing an at least biphasic mixture by mixing the first liquid phase with the second liquid phase;
a first feed by means of which the first reservoir vessel is in fluid communication with the active element;
a second feed by means of which the second reservoir vessel is in fluid communication with the active element;
a collection vessel for accommodating the mixture;
a discharge by means of which the active element is in fluid communication with the collection vessel;
a pump which is incorporated in the discharge in such a way that the mixture is conveyable by the pump from the active element via the discharge into the collection vessel.

According to the invention the apparatus has the features:
that the first feed and the second feed are vertically oriented at least on a vertical section;
that on the vertical section the second feed is arranged inside the first feed;
and that on the vertical section the first feed or the second feed or both feeds are axially displaceable such that the axial position of the second feed relative to the first feed is adjustable.

The apparatus according to the invention is characterized by a vertical orientation of the feeds leading to the active element: The first and the second feed are both arranged vertically at least in one section upstream of the active element, so that the flows through the feeds are oriented in the direction of acceleration due to gravity. The section in which the feeds run vertically is referred to here as the vertical section. This is not a distinct constructional element of the apparatus but rather a region of the apparatus in which the feeds extend vertically. Since the flow direction through the vertical section is parallel to acceleration due to gravity—i.e. downwards—and the active element is arranged downstream of its feeds, logic dictates that the vertical section extends above the active element. However, the vertical section need not be arranged perpendicularly above the active element since the feeds may also be horizontal or inclined outside the vertical section. However, the vertical section is preferably arranged perpendicularly above the active element; it is particularly preferable when the vertical section extends up to the active element, so that the liquid phases enter the active element vertically. In this constellation the flow vectors are oriented parallel to the gravitational vector.

A further essential feature of the apparatus according to the invention is that the second feed is conducted inside the first feed on the vertical section. This means that the second feed is surrounded by the first feed. The wall of the second feed thus contacts the second liquid phase on the inside and the first liquid phase on the outside. The wall of the first feed contacts the first liquid phase on the inside and the environment on the outside.

The vertical orientation of the feeds and their nested arrangement has a positive effect on the flow conditions in the active element which results in a particularly homogeneous mixing of the phases. In addition, the flow ratios brought about by this configuration have proven particularly stable when the flow cross sections are varied. Operating conditions optimized for small flow cross-sections are therefore also retained in the course of a scale up.

In principle the active element of the apparatus forms a thin film for mixing mass transfer. The ratio of capillary flow and edge flow of the buffer medium is relevant. The produced thin film (telescope antenna effect) undergoes mixing substantially by diffusion without occurrence of fouling and blocking at the interface. Since in the apparatus according to the invention the flows need not be "squeezed" through microstructures the procedure proceeds virtually pressurelessly, thus allowing simple scale up of the arrangement and the process.

A further design element of the invention provides that the first and/or the second feed are axially displaceable on the vertical section, so that the axial position of the two feeds relative to one another may be adjusted. Varying the axial orientation allows the flow conditions inside the active element to be adjusted, thus allowing the mixing result to be optimized.

The pump of the apparatus is preferably a centrifugal pump which comprises a housing and a rotor (impeller) which is rotatably mounted in the housing around a rotational axis and is rotatably propellable via a propulsion means. In the simplest case of the means of propulsion is a motor which is mechanically coupled to the rotor of the pump via a shaft. A preferred variant provides for magnetic force transfer or a mechanical shaft. In both cases the rotational axis of the rotor is preferably vertical.

The fact that the rotational axis of the centrifugal pump runs vertically means that the centrifugal pump accelerates the mixture in the horizontal plane. The fact that the liquid phases flow through the vertical section in the falling direction and are then accelerated horizontally after mixing means that the liquids are deflected by 90° in their flow path through the feeds, the active element and the pump.

This intensifies the mixing. The centrifugal pump thus also assumes part of the mixing task; it is effectively a second mixing stage. In the case of a vertical arrangement of the rotational axis the rotor can also be destabilized a little, thus also allowing the pump to be utilized for quenching. Furthermore, in the case of a coaxial orientation of the rotational axis and the axis of the vertical section the mixture may be introduced in regions of the housing where it is conveyed by wall flow. This also has a positive effect on product formation.

All these design elements according to the invention result in a particularly intensive mixing of the liquid phases, so that the components present therein are brought into particularly intimate contact with one another and can interact efficiently. The intensive diffusion processes brought about by the large differences in velocity ensure fine distribution of the nanoscale substances in the dispersion medium. The result is a mixture in which the nanocarrier/the nanoformulation has a particularly narrow particle size distribution.

A further advantage of the apparatus according to the invention is its simple and robust construction. This increases reliability. In addition, the apparatus may be operated both batchwise and continuously. Thus, in the same apparatus the production process may be initially optimized in batch operation before the production throughput is raised in simple fashion by switching to continuous operation. Furthermore, the flow conditions in the active element have proven particularly stable, so that increasing the diameter in the course of a capacity expansion leads to the occurrence of only very few similarity effects which impair product quality. The apparatus according to the invention thus makes it possible to perform a real scale up to expand capacity. This allows particularly economic transfer of findings from experimental operation to industrial production scale.

Ultimately the apparatus according to the invention makes it possible to develop processes cost-effectively and effect production with consistently high quality. The invention thus allows particularly economic production.

A further advantage of the apparatus according to the invention is that its active element eschews microstructured components and is therefore less susceptible to fouling and blockages.

A preferred development of the apparatus provides that the first feed inside the vertical section is formed from a first linear pipeline, in that the second feed inside the vertical section is formed from a second linear pipeline and in that the first linear pipeline and the second linear pipeline extend coaxially on the vertical section. In this embodiment the feed conduits are in the form of fixed pipelines and run coaxially at least on the vertical section. The solid pipelines allow particularly stable flow conditions and precise axial positionability. Outside the vertical section the feed conduits may also be flexible, for instance in the form of a hose line. This may also be necessary in the interest of axial displaceability. The coaxiallity, i.e. the central arrangement of the second feed conduit in the first feed conduit, allows a particularly stable flow profile in the active element.

It is preferable when the second linear pipeline is in the form of a capillary having a much smaller cross section relative to the cross section of the first linear pipeline. The reason for this is that according to the invention the flow (volume flow) through the first feed is much greater than the addition amount of the second liquid phase. The first and the second linear pipeline preferably both have a circular cross section. It is also possible for the second feed conduit to be dualized, i.e. composed of two pipelines or capillaries running in parallel, each of which conduct half of the volume flow of the second liquid phase.

In its simplest configuration the apparatus according to the invention merely allows production of a biphasic mixture of the first liquid phase and the second liquid phase (binary system). However, several variants are also possible in which the apparatus allows production of an at least triphasic mixture from a first, second and third liquid phase (tertiary system).

Embodiments of the apparatuses capable of producing only biphasic mixtures are herein referred to as "binary apparatuses" while apparatuses allowing production of triphasic mixtures are referred to as "tertiary".

Every variant of the tertiary apparatus necessarily comprises a third reservoir vessel for accommodating a third liquid phase and a third feed by means of which the third reservoir vessel is in fluid communication with the active element, wherein the active element is adapted for providing an at least triphasic mixture by mixing the first liquid phase with the second liquid phase and the third liquid phase and wherein the first feed inside the vertical section is formed from a first linear pipeline, the second feed inside the vertical section is formed from a second linear pipeline and the third feed inside the vertical section is formed from a third linear pipeline. In line with the general inventive concept the third feed is vertically oriented at least on the vertical section, on the vertical section said feed is arranged inside the first feed, and the third feed is axially displaceable on the vertical section such that the axial position of the third feed relative to the first feed is adjustable. The third feed therefore fulfills the same design features as the second feed.

In a first variant of a tertiary apparatus the second pipeline and the third pipeline run parallel to one another through the first pipeline. In the simplest case this means that the wall of the third pipeline contacts the third liquid phase on the inside and the first liquid phase on the outside. (The wall of the second feed still contacts the second liquid phase on the inside and the first liquid phase on the outside.) The second and the third pipeline are preferably each configured as a capillary having a smaller cross section than the outer pipeline. In this constellation the pipelines cannot be oriented coaxially. This construction of a tertiary apparatus is in principle identical to a binary apparatus having a dualized second pipeline.

In a second, preferred variant of a tertiary apparatus the second pipeline and the third pipeline may run parallel to one another through the first pipeline. The three pipelines are then not coaxial. The first pipeline may then also have an annular cross section: This is achieved by providing the first pipeline with a separate inner wall. The first liquid phase then flows through the annular gap formed between the inner wall and the outer wall. The first pipeline is then provided with a core which does not have a first liquid phase flowing through it. The second and the third pipeline are then passed through the core. The core remains empty between the outer wall of the second and the third pipeline and the inner wall of the first pipeline.

However, in a third variant of a tertiary apparatus all three pipelines may extend coaxially on the vertical section. This is possible when on the vertical section the third feed is arranged inside the second feed while the second feed still extends inside the first feed. The third pipeline is thus surrounded by the first and by the second pipeline while the second pipeline is surrounded only by the first pipeline. The wall of the third pipeline contacts the third liquid phase on the inside and the second liquid phase on the outside. The wall of the second pipeline contacts the second liquid phase on the inside and the first liquid phase on the outside. The wall of the first pipeline contacts the first liquid phase on the inside and the environment on the outside. In this three-fold nested constellation all three pipelines may extend coaxially but need not do so. However, a coaxial arrangement is preferred in the interest of a stable mixture. This threefold nested variant entails somewhat greater apparatus complexity than the first variant with parallel second and third pipelines but achieves better homogeneity of mixing.

In a preferred development of the invention the rotational axis of the rotor is oriented coaxially to the axis of the first feed in the region of the vertical section. This means that the pump, more precisely its rotor, must be arranged below the active element. The mixture flowing out of the active element passes directly onto the rotor and is accelerated horizontally outwards there. The pump rotor thus acts as an additional mixer which effects fine distribution of the components in the dispersion. In this constellation the discharge from the pump is preferably to be implemented horizontally at least in sections. There is then a right angle between the feed and the discharge. The flow is deflected by 90° inside the pump. This constellation allows for destabilization of the rotor which results in a small amount of recirculation which has a positive effect on the product.

In a further preferred embodiment of the apparatus the pump is levitronic. This is to be understood as meaning that the rotor is magnetically mounted and the propulsion means is a rotating field. The rotating field rotates the rotor of the pump and thus allows power transmission from the propulsion means to the rotor without mechanical contact between the propulsion means and the rotor. In this constellation the rotor of the pump is simultaneously the rotor of an electric motor; the housing of the pump is simultaneously the stator of the electric motor. The pump and the propulsion means are integrated. The advantage of this construction is that the housing need not be perforated by a drive shaft since no drive shaft exists. Instead of mechanical power transmission via a drive shaft power transmission in a levitronic pump is effected purely magnetically via the rotating field. The rotating field may optionally also effect the mounting of the rotor in the housing. This not only does away with a failure-prone seal of the drive shaft but also allows the mixture to flow on both sides of the rotational plane of the rotor since there is no drive shaft blocking flow on either side. A further advantage of levitronic centrifugal pumps is that they may be operated so as to minimize cavitation effects, thus resulting in less material abrasion or spalling which could contaminate the mixture.

Levitronic pumps are commercially available such as for example the pump type PuraLev-i30 from Levitronix GmbH, Zurich, CH.

One advantage of the apparatus according to the invention is that it may be easily converted from batch operation to continuous operation. This requires only recycling the discharge back into the first reservoir vessel to form a circuit (loop) from the first reservoir vessel through the first feed into the active element, through the pump and back into the first reservoir vessel. The collection vessel and the first reservoir vessel are then identical and the discharge is in the form of a circuit. This constitutes a particularly preferred embodiment of the invention. In this constellation the products are either withdrawn from the first reservoir vessel or discharged from the circuit after a certain running time of the apparatus. The circuit need not necessarily be closed: It is also possible to circulate a relatively large liquid volume through the circuit in the apparatus while simultaneously discharging a relatively small amount of product from the discharge. The reservoir vessels are then simultaneously replenished with fresh liquid phase according to the withdrawn amount. Such a process mode is a hybrid form of continuous operation and batch operation.

The volume flow of the first liquid phase is generally markedly greater than that of the second and/or third liquid phase. To control the volume flow of the first liquid phase it is therefore sufficient to adjust the volume flow of the pump. The volumes of the first and/or second liquid phases are then negligible. In the simplest case the apparatus thus comprises a pump with an adjustable conveying volume. The conveying volume of the pump should be under open- or closed-loop control. Adjusting the conveying volume is most easily done via the speed of propulsion, i.e. of the rotating field which rotates the rotor of the pump/the motor.

For exact adjustment of the mixing ratios, the apparatus should comprise at least one metering apparatus which is adapted for metering the second liquid phase into the active element. Since the volume flow of the second liquid phase is markedly smaller than that of the first liquid phase the metering apparatus may be a linear piston pump in a preferred variant. The capacity of a piston pump is in principle limited by the piston volume. This is not particularly disruptive in batch operation but is in continuous operation. Therefore in continuous operation a plurality of piston pumps which alternately effect metered addition of the same phase should be provided. One piston is raised while the other piston effects metered addition. The same effect may be achieved using a piston pump comprising a plurality of pistons.

A tertiary apparatus should also include a corresponding metered addition apparatus for metered addition of the third liquid phase into the active element. What is specified above in connection with the metered addition apparatus for the second liquid phase applies correspondingly.

It is preferable when the conveying stream of a metered addition apparatus, in particular of all metered addition apparatuses, is adjustable. For piston pumps adjustment of the volume flow is effected by adjustment of the speed of the linear drive.

It is particularly preferable when the volume flows of the centrifugal pump and of the metered addition apparatus(es) are controlled by a central control unit of the apparatus.

The present invention also provides a process for producing nanocarriers and/or nanoformulations which is performed using the apparatus specified here. A production process according to the invention comprises the steps of:
  providing an apparatus according to the invention,
  providing a first liquid phase in the first reservoir vessel, wherein the first liquid phase contains a first liquid dispersion medium;
  providing a second liquid phase in the second reservoir vessel, wherein the second liquid phase is a second liquid dispersion medium and contains at least one component selected from the group consisting of precursor to a nanocarrier, precursor to an active ingredient, active ingredient;
  propelling the pump to establish a liquid flow from the first reservoir vessel via the first feed into the active element and via the discharge into the collection vessel;
  metering the second liquid phase via the second feed into the active element, wherein the volume flow of the second liquid phase in the second feed is smaller than the volume flow of the liquid flow in the first feed;
  mixing the first liquid phase and the second liquid phase in the active element to obtain a mixture containing a nanocarrier and/or a nanoformulation;
  collecting the mixture in the collection vessel;
  withdrawing the mixture from the apparatus.

The mixture is optionally subjected to a further workup in a further step. The workup may comprise in particular sterile filtration or separation of the nanocarrier and/or the nanoformulation from the mixture.

The process is performed in a single run until a sufficient amount of nanocarriers/nanoformulation has accumulated in the collection vessel. The mixture is then withdrawn from the apparatus. If required, the mixture is subjected to a further workup. The workup in particular comprises withdrawing the actual target product—the nanocarriers/the nanoformulation—from the mixture. The separation is effected by prior art methods through evaporation of the liquid dispersion medium or through filtration, for example tangential flow filtration or through membrane technology or through combinations thereof. Further suitable separation methods include dialysis, sterile filtration, spray drying or lyophilization.

The tertiary apparatus may be used to produce a tertiary mixture, thus making a broader product spectrum available. An accompanying production process comprises the steps of:

providing a first liquid phase in the first reservoir vessel, wherein the first liquid phase contains a first liquid dispersion medium and wherein the pH of the first liquid phase is in particular between 6 and 8, preferably 7;

providing a second liquid phase in the second reservoir vessel, wherein the second liquid phase contains a second liquid dispersion medium and at least one precursor to an active ingredient and/or to a nanocarrier and wherein the pH of the second liquid phase is in particular between 3 and 5, preferably 4;

providing a third liquid phase in the third reservoir vessel, wherein the third liquid phase comprises a third liquid dispersion medium and at least one further component, wherein the further component is selected from the group consisting of precursor to a nanocarrier, active ingredient, precursor to an active ingredient;

propelling the pump to establish a liquid flow from the first reservoir vessel via the first feed into the active element and via the discharge into the collection vessel;

mixing the first liquid phase and the second liquid phase and the third liquid phase by metering the third liquid phase via the third feed into the active element, wherein the volume flow of the third liquid phase in the third feed is smaller than the volume flow of the liquid flow in the first feed.

The production of tertiary systems is of interest especially in the production of LNP.

An essential aspect of the process for producing tertiary mixtures is that the first and the second liquid phase have different acidities. The first liquid phase is closer to neutral and has a stronger buffer capacity than the second liquid phase; its pH is 6 to 8, preferably 7, while the second liquid phase is more acidic with a pH of 3 to 5, preferably pH 4. Since the volume flow of the first liquid phase is greater than the volume flow of the second liquid phase the active element experiences abrupt rebuffering of the precursors present in the second liquid phase from acidic to neutral. This in-situ rebuffering in the active element is a particular distinguishing feature relative to conventional processes carried out in a T- or Y-shaped mixer: In these conventional processes mixing is followed by a separate step of stabilization because the nanocarriers are not stable for long in the milieu of the mixture. The process according to the invention omits this step on account of its in-situ rebuffering: The in-situ rebuffering establishes a milieu in which the nanocarriers are stable for longer directly in the active element. In conjunction with the diffusion processes occurring in the active element the precursors present in ionized form are combined into nanocarriers. In the case of LNPs the lipids are cationically charged for a short time in contact with the second liquid phase (pH 4) and bind the anionic RNA or DNA from the second liquid phase. The mixture is then directly captured by the first liquid phase and the pH 7 present here dominates as a result of the higher buffer capacity in this medium, thus immediately stabilizing the particles. If active ingredients are present in the first or second liquid phase the nanocarriers are also loaded with active ingredient as a result of these effects. The great difference in the flow rate in the active element has the result that the nanocarriers/the nanoformulation are finely distributed in the discharge, thus achieving a homogenous particle size distribution in the range of just a few hundred nanometers.

The first liquid phase and the second liquid phase differ not only in their acidity but also in their chemical nature: The first liquid phase may have a rather inorganic character while the second and/or third liquid phase is organic. It is preferable when the first two liquid phases are aqueous with different acidities and the third liquid phase is organic. In this way it is possible to use precursors and active ingredients soluble in different media: For instance, water-soluble active ingredients may be loaded onto carriers whose precursors are soluble only in organic solvents or vice versa. Examples of water-soluble active ingredients include peptides, proteins, DNA and RNA such as in particular (m)RNA or siRNA. The lipids employed as carriers (liposomes, LNP) or polymers (particles, polyplexes) are dissolved in organic solvents such as for example ethanol or acetonitrile. In such cases the first dispersion medium is water while the second dispersion medium is an organic substance. In a tertiary system the first and the second dispersion medium is usually water while the third dispersion medium is an organic system.

Suitable organic substances include in particular monohydric alcohols such as ethanol for example or a polyhydric alcohol such as glycerol for example. Alternatively employable as the organic substance are acetonitrile or dimethyl sulfoxide (DMSO).

One example of a precursor to a nanocarrier which is soluble in organic solvents such as ethanol or glycerol is phosphatidylcholine (lecithin). The phosphatidylcholine may be obtained from egg or from soy. Further examples of precursors for nanocarriers which are soluble in organic solvents include cholesterol, 1,2-dioleyloxy-3-dimethylaminopropane (DODMA), polyethylene glycol dimethacrylate (PEG-DMA) and distearoyl phosphatidylcholine (DSPC).

For pH adjustment the first liquid phase may contain a buffer. The buffer ensures a milieu in which a precursor is stable. The buffer may also be chosen such that the acidity of the mixture, i.e. after the mixing of the first and the second liquid phase, has the desired value. This allows corresponding control of the process of rebuffering. In the case of an aqueous first liquid phase the buffer may be selected from the group consisting of ammonium sulfate, acetate, polyvinyl alcohol, phosphate, 2-(4-(2-hydroxyethyl)-1-piperazinyl)-ethanesulfonic acid.

In a preferred development of the process with at least one aqueous and one organic phase the first (aqueous) liquid phase contains a buffer and the second liquid phase (organic) contains an active ingredient or a precursor to an active ingredient. It is preferable when the buffer is polyvinyl alcohol and the organic substance is acetonitrile. The selected precursor to the nanocarrier is then a polylactide-co-glycolide which is readily soluble in acetonitrile. However, it is also possible to dissolve active ingredients in acetonitrile, for instance ritonavir. As an alternative to acetonitrile it is possible to employ acetone or dimethyl sulfoxide or ethyl acetate as the organic solvent.

Also possible are process variants where the first liquid phase (aqueous) contains a buffer and where the second liquid phase (alcoholic) contains two precursors to a nanocarrier. Thus for example the buffer may be ammonium sulfate while the two precursors to the nanocarrier are Lipoid E PC and Cholesterol HP.

In tertiary systems comprising a first aqueous phase, a second aqueous phase and an organic phase the second aqueous phase may also contain a species which is both a first precursor to a nanocarrier and the precursor to an active ingredient. A second precursor to the nanocarrier is then dissolved in the third (organic) phase. This constellation is employed in the production of nanoformulations where DNA or (m)RNA is carried on LNP. The water-soluble DNA/(m)RNA is dissolved in the second aqueous phase under acidic conditions. Lipids are dissolved in the organic phase. The two are contacted in the active element and dispersed in the first liquid phase (aqueous neutral) and simultaneously rebuffered. The DNA/(m)RNA is both the active ingredient and a precursor to the nanocarrier.

Independently of the chemical nature of the liquid phase the process may be performed continuously when the discharge of the apparatus is in the form of a circuit and the first reservoir vessel simultaneously functions as a collection vessel. The process management is then carried out such that the first liquid phase is initially circulated before the second liquid phase is metered in. It is also possible for product to be continuously withdrawn while the first liquid phase and optionally also further liquid phases is/are circulated in the circuit. At least the second liquid phase is then likewise continuously replenished. Thus in this embodiment the second liquid phase is supplied while at least the first phase is circulated. It is preferable when the volume flow of the liquid amount circulated in the circuit is greater than the withdrawn product amount. The replenished reactant amount preferably corresponds to the withdrawn product amount, so that the total amount in the system remains constant. The same applies to tertiary systems.

The process according to the invention made possible by the apparatus according to the invention results in a product of high quality. The product especially features a particularly homogenous particle size distribution and optionally also a uniform active ingredient concentration. The product of the process is a nanocarrier or a nanoformulation.

The obtained product is nanoscale. It has an average particle size smaller than 300 nm, preferably smaller than 200 mm, particularly preferably between 40 nm and 140 nm. A particular type of nanocarrier is always accompanied by a certain order of magnitude of particle size. Particle size distribution is measured by the principle of dynamic light scattering with a Zetasizer instrument from Malvern Panalytical Ltd, GB.

The obtained product has a polydispersity index between 0.08 and 0.2. This indicates a uniform product quality. The polydispersity index (PDI) is measured by the principle of dynamic light scattering with a Zetasizer instrument from Malvern Panalytical Ltd, GB. A PDI of 0.1 to 0.3 is particularly preferred.

The process allows production of nanoformulations having a high active ingredient concentration. It is preferable when the active ingredient concentration by mass in the nanoformulation according to the invention is from 1 ppm to 50%. This value is measured by means of: HPLC-UV, for example using an AGILENT 1260 series apparatus. The large range of possible active ingredient concentrations results from the fact that some active ingredients, for example mRNA, are administered in very low doses.

It is also possible to produce a product having a high active ingredient concentration because the process achieves a high loading efficiency. This means that the active ingredient provided is to a large extent loaded onto the nanocarrier and not lost.

Surprisingly, it has been found that present apparatus for preparing a nanocarrier and/or nanoformulation is suitable for preparing microcarrier and/or microformulations as well.

In the context of the present invention a microcarrier is a composition for carrying pharmaceutical, cosmetic or nutraceutical active ingredients. The microcarrier may consist of a pure substance or may be a mixture of two or more substances. The substances may be solid, semi-fluid or liquid. The substances may be single-phase or multi-phase substances: In all cases microcarriers are in particulate form, wherein the average particle size is larger than 1 µm and smaller than 1000 µm.

Hence, a microcarrier in the sense of present invention is similar to a nanocarrier, except of the size.

Examples for microcarrier are polymeric particles having a particle size ranging from 1 µm to 100 µm or from 20 µm to 90 µm. In particular, biodegradable polymeric particles of that size ranges are used as carrier for pharmaceuticals, nutraceuticals or cosmetics.

As similar as nanoformulations are based on nanocarriers, microformulations are based on microcarriers:

Thus, in the context of the present invention a microformulation is a dosage form of a pharmaceutical, cosmetic or nutraceutical active ingredient carried by a microcarrier. The active ingredient may be on the surface of the microcarrier, may be inside the microcarrier or may be complexed with the microcarrier.

The finding, that present apparatus for preparing nanocarriers and/or nanoformulations is suitable for preparing microcarriers and/or microformulations is surprising, as resulting particles are more than three times as large as the nanoparticles.

Hence, a further object of the present invention is the use of present apparatus for preparing microcarrier and/or microformulations.

In particular, the following method is a further object of the invention:

A process for producing a microcarrier and/or a microformulation, comprising the steps of:
a) providing an apparatus according to the invention;
b) providing a first liquid phase in the first reservoir vessel, wherein the first liquid phase contains a first liquid dispersion medium;
c) providing a second liquid phase in the second reservoir vessel, wherein the second liquid phase is a second liquid dispersion medium and contains at least one component selected from the group consisting of precursor to a microcarrier, precursor to an active ingredient, active ingredient;
d) propelling the pump to establish a liquid flow from the first reservoir vessel via the first feed into the active element and via the discharge into the collection vessel;
e) metering the second liquid phase via the second feed into the active element, wherein the volume flow of the second liquid phase in the second feed is smaller than the volume flow of the liquid flow in the first feed;
f) mixing the first liquid phase and the second liquid phase in the active element to obtain a mixture containing a microcarrier and/or a microformulation;
g) collecting the mixture in the collection vessel;
h) withdrawing the mixture from the apparatus;
i) optionally: working up the mixture, in particular separating the microcarrier and/or the microformulation from the mixture.

Products of this inventive process are microcarriers with a particle range from 1 µm to 1000 µm and/or microformultations based thereon. Preferably, the particle size ranges from 1 µm to 100 µm or from 20 µm to 90 µm.

The preferred embodiments of inventive process for preparing microcarriers and/or microformulations are analogons to preferred embodiments of inventive process for preparing nanocarriers and/or nanoformulations.

BRIEF DESCRIPTION OF THE DRAWINGS

The processes according to the invention shall now be elucidated with reference to exemplary embodiments. To this end.

DETAILED DESCRIPTION OF THE INVENTION

Figure 1:
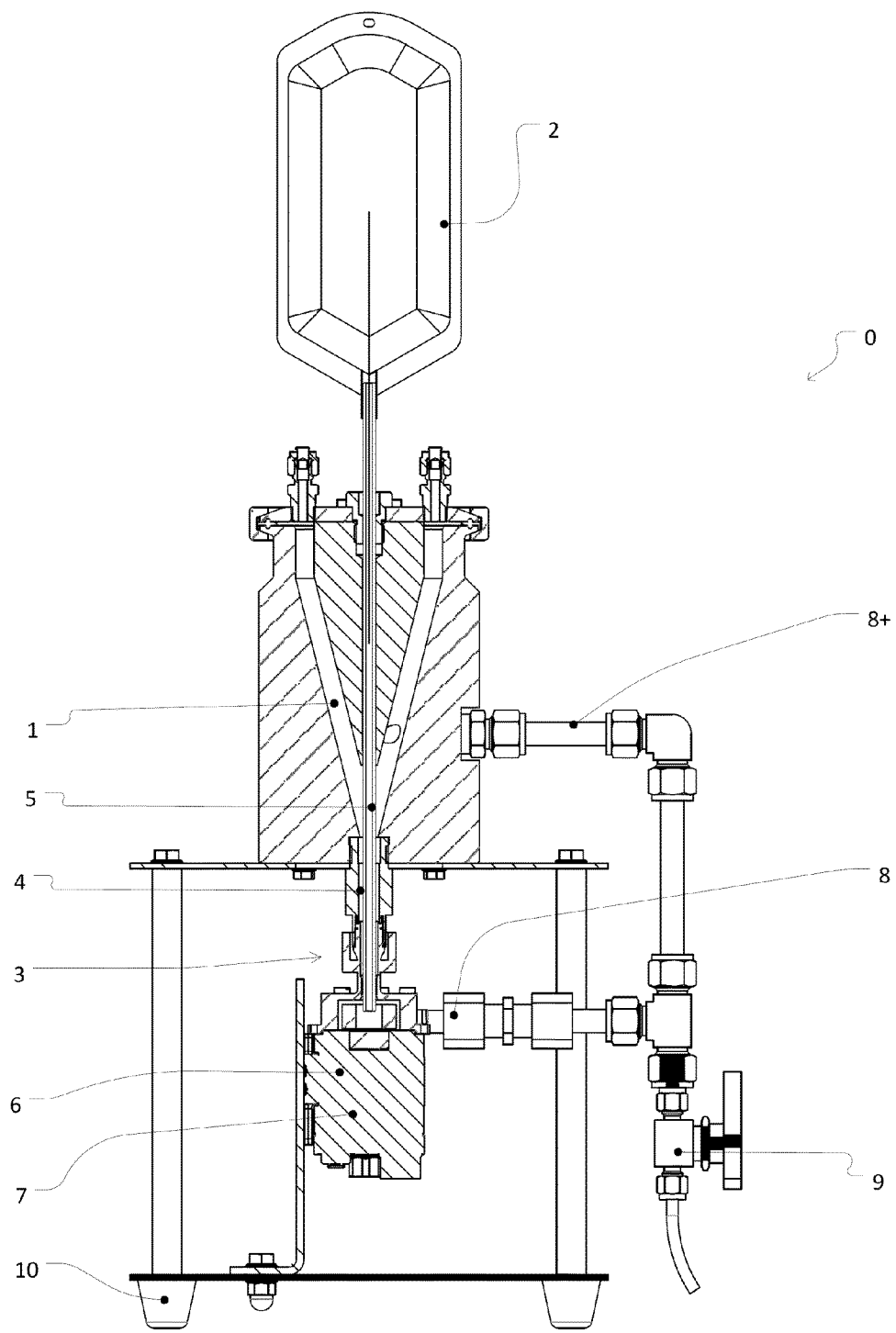
FIG. 1: shows a first variant of an apparatus according to the invention

FIG. 1 shows an overview of a first inventive apparatus 0. It comprises a first reservoir vessel 1 in the form of a funnel-shaped tank and a second reservoir vessel 2 in the form of a plastic bag. The two reservoir vessels 1, 2 are used for accommodating a first and second liquid phase. The volume of the first reservoir vessel 1 is markedly greater than the volume of the second reservoir vessel 2.

The liquid phases are each dispersions containing a liquid dispersion medium and precursors to nanocarrier and/or active ingredients.

An active element 3 is arranged below the reservoir vessels 1, 2 (vertically in the direction of acceleration due to gravity). The active element 3 serves to mix the two liquid phases. A first feed conduit 4 and a second feed conduit 5 connect the first reservoir vessel 1/the second reservoir vessel with the active element 3. The liquid phases can flow from their respective reservoir vessels 1, 2 through the respective feed 4, 5 to the active element 3. Both feed conduits 4, 5 extend vertically.

A pump 6 is arranged below the active element 3 (vertically in the direction of acceleration due to gravity). The pump 6 is used to circulate the mixture provided by the active element 3. The active element 3 and the pump 6 are directly connected. The pump 6 may be rotatably propelled by an integrated propulsion means 7.

Provided downstream of the pump 6 is a discharge 8 which extends horizontally for a distance before returning to the first reservoir vessel 1. The discharge 8 is therefore configured as circuit 8+. The discharge 8 is provided with a withdrawal fitting 9.

The entire apparatus 0 is accommodated in a frame 10. A control means and a metered addition apparatus for metered addition of the second liquid phase are not shown. The control means controls the volume flow of the pump 6 and the volume flow of the metered addition apparatus. The volume flow of the pump 6 corresponds to the volume flow of the mixture of the first and second liquid phase through the discharge 8 configured as a circuit. In the mixture the proportion of the first liquid phase is markedly greater than the proportion of the second liquid phase. The volume flow of the pump thus corresponds to the volume flow of the first liquid phase (neglecting the second liquid phase). The pump is thus effectively a type of metered addition apparatus for the first liquid phase.

In operation the pump 6 initially establishes a circuit of the first liquid phase from the first reservoir vessel 1, through the first conduit 4 into the active element 3 and through the discharge 8/circuit 8+ back into the first reservoir vessel 1. A small amount of the second liquid phase from the second reservoir vessel 2 is then metered into the active element 3 via the second feed conduit 5. The two phases are mixed in the active element 3 to form a mixture. The mixture contains dispersion medium and, dissolved therein, nanocarrier or nanoformulation which is formed by contact of the precursors in the active element 3.

The circuit is operated until a desired amount of product has accumulated in the mixture. The mixture is then withdrawn via the withdrawal fitting 9 and the product separated from the mixture. This is carried out outside the apparatus 0 with known separation apparatuses. It is also possible to withdraw the mixture from the circuit continuously.

FIG. 2A shows a tertiary embodiment of the apparatus 0. This allows production of mixtures from three liquid phases The first liquid phase is filled into the first reservoir vessel 1 which is again funnel-shaped, like a silo. Accordingly, the first reservoir vessel has the shape of a cone 11 on the inside. The angle of the cone 11 may be selected according to the viscosity of the first liquid phase. In FIG. 2A the angle is 29° and in FIG. 3 the angle is 55° but angles up to 86° are also conceivable. The volume of the first reservoir vessel 1 is limited by an insert 111. The insert 111 is likewise conical and has the same angle as cone 11. The insert 111 may be installed axially offset to vary the volume of the first reservoir vessel 1. This is especially necessary when the apparatus 0 is used for production of different nanoformulations which differ in their active ingredient concentration. In recirculating operation the holdup of the first reservoir vessel may also be adjusted via the insert 111. The first reservoir vessel 1 is also provided with two charging fittings 1111 through which the reservoir vessel may be filled or replenished with first liquid phase. The apparatus 0 allows continuous operation by continuously supplying the first liquid phase via the charging fittings 1111. At the foot of the cone 11 the first reservoir vessel transitions into a first pipeline 12. This is readily apparent in the magnified view of FIG. 2B.

The reservoir vessels for the second and third liquid phase are not shown in FIG. 2A. However, a second pipeline 14 and a third pipeline 15, which serve as a feed for second liquid phase (via pipeline 14) and third liquid phase (via pipeline 15) into the active element 3, are shown.

Accordingly, the two pipelines 14 and 15 extend along the full length of the apparatus to the active element 3. Between the foot of the cone 11 and the active element 3 the second pipeline 14 and the third pipeline 15 extend vertically and inside the first pipeline 12. This region is referred to as the vertical section because all three pipelines 12, 14 and 15 extend in the direction of acceleration due to gravity. The flow vectors of the three liquid phases immediately before contact thereof in the active element is thus parallel to the gravitational vector.

The pipelines 14 and 15 moreover also run parallel and vertical above the foot of the cone 11 but this is not relevant. FIG. 2C shows a cross section through the second and third pipelines 14, 15 above the vertical section. The shaded component shown in FIG. 2C is a sheathing.

At their respective openings in active element 3 the two pipelines 14 and 15 have each been provided with a V-shaped ground end 13. This is more easily apparent in FIG. 2B. The angle of the ground end 13 may be 15° or 30° or 60°.

It is also conceivable to pass second liquid phase through both the second pipeline 14 and the third pipeline 15. The second and the third pipeline are then each one conduit element of a dualized second feed conduit of a binary apparatus for producing a biphasic mixture.

Figure 2A:
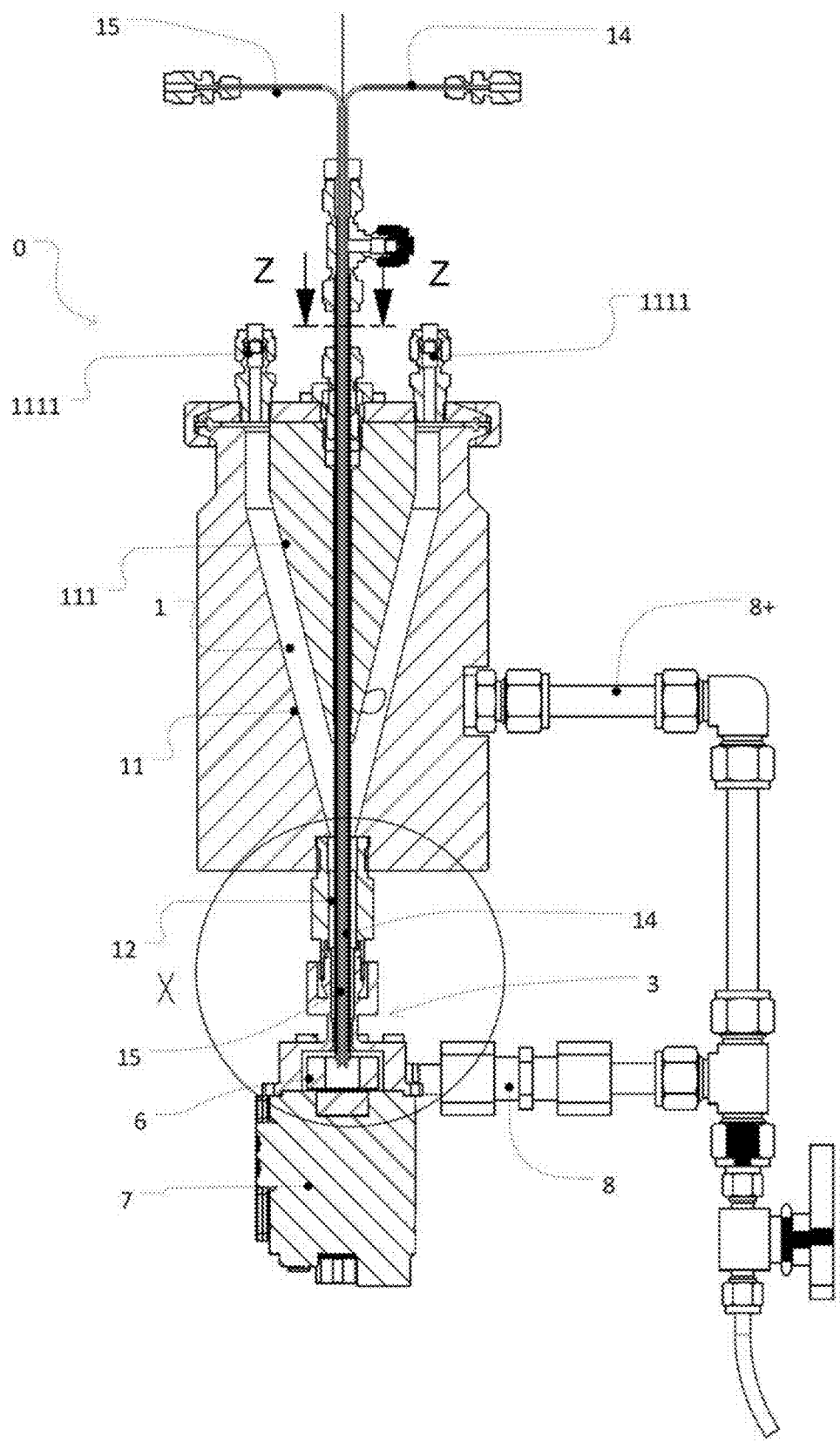
FIG. 2A: shows a second variant of an apparatus according to the invention.
Figure 3:
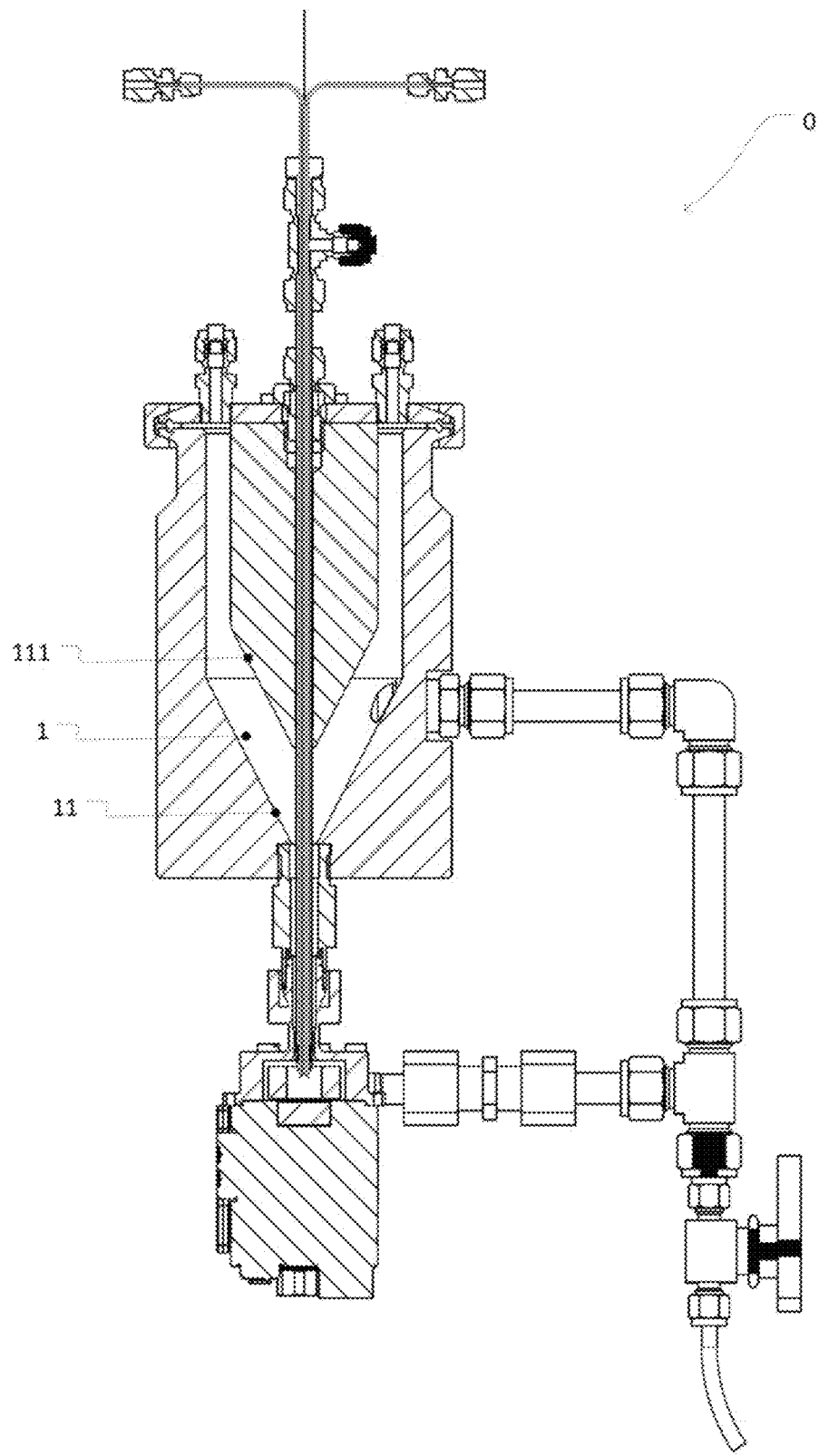
FIG. 3: shows a third variant of an apparatus according to the invention.

FIG. 3 shows a third inventive embodiment of the apparatus 0. It corresponds substantially to the second variant shown in FIG. 2A. However, the difference is in the volume of the first reservoir vessel 1 which is greater in the variant shown in FIG. 3 than in FIG. 2A. The greater volume has been established by positioning the insert 111 further upwards. This enlarges the space between the cone 11 of the first reservoir vessel and the corresponding cone of the insert 111. Furthermore, the cone angle in the variant shown in FIG. 3 is greater; it is 55° here instead of only 29° in FIG. 2A.

Figure 4A:
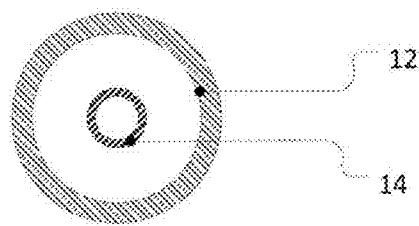
FIG. 4A: shows a cross section of a vertical section of a binary apparatus, schematic view.
Figure 4B:
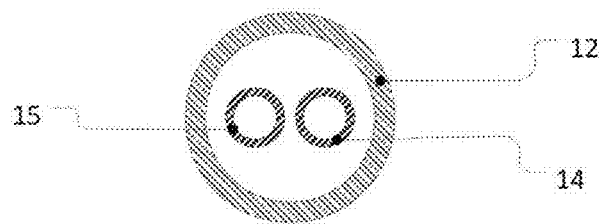
FIG. 4B: shows a cross section of a vertical section of a 1st variant of a tertiary apparatus, schematic view.

FIGS. 4A to 4B show a schematic view of possible embodiments of the vertical section in cross section, i.e. in the perspective of acceleration due to gravity. All pipelines 12, 14, 15 are shown as circular but may also be angular.

The vertical section shown in FIG. 4A belongs to a binary apparatus having a first pipeline 12 for the first liquid phase and a second pipeline 14 for the second liquid phase. The second pipeline 14 extends inside the first pipeline 12. Both pipelines are arranged coaxially, i.e. the geometric center of their cross-sections is identical. The first liquid phase flows inside the first pipeline 12 and outside the second pipeline 14. The second liquid phase flows inside the second pipeline 14. The constellation shown in FIG. 4A is also referred to as "single capillary".

The vertical section shown in FIG. 4B referred to as "dual capillary" belongs to a tertiary apparatus having a first pipeline 12 for the first liquid phase, a second pipeline 14 for the second liquid phase and a third pipeline 15 for the third liquid phase. The second pipeline 14 extends inside the first pipeline 12 and the third pipeline 15 likewise extends inside the first pipeline 12. The second pipeline 14 and the third pipeline 15 are parallel. The first liquid phase flows inside the first pipeline 12 and outside the second pipeline 14 and the third pipeline 15. The second liquid phase flows inside the second pipeline 14. The third liquid phase flows inside the third pipeline 15. It is also conceivable to pass the same second liquid phase through both the second pipeline 14 and the third pipeline 15. The apparatus with the dual capillary is then utilized merely in binary fashion.

Figure 4C:
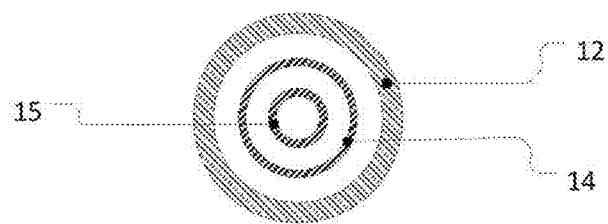
FIG. 4C: shows a cross section of a vertical section of a 2nd variant of a tertiary apparatus, schematic view.

The vertical section shown in FIG. 4C belongs to a tertiary apparatus having a first pipeline 12 for the first liquid phase, a second pipeline 14 for the second liquid phase and a third pipeline for the third liquid phase. The second pipeline 14 extends inside the first pipeline 12 and the third pipeline 15 likewise extends inside the first pipeline 12 and, in addition, also inside the second pipeline 14. All pipelines 12, 14, 15 are arranged coaxially to one another. The first liquid phase flows inside the first pipeline 12 and outside the second pipeline 14. The second liquid phase flows inside the second pipeline 14 and outside the third pipeline 15. The third liquid phase flows inside the third pipeline 15.

Figure 4D:
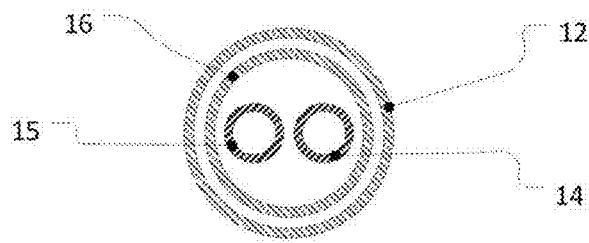
FIG. 4D: shows a cross section of a vertical section of a 3rd variant of a tertiary apparatus, schematic view.

The vertical section shown in FIG. 4D belongs to a tertiary apparatus having a first pipeline 12 for the first liquid phase, a second pipeline 14 for the second liquid phase and a third pipeline for the third liquid phase. The second pipeline 14 extends inside the first pipeline 12 and the third pipeline 15 likewise extends inside the first pipeline 12. The second pipeline 14 and the third pipeline 15 are parallel. The first pipeline 12 here comprises an inner wall 16. The flow cross section of the first pipeline is therefore circular. The first liquid phase flows outside the inner wall 16 of the first pipeline 12 and inside the outer wall of the first pipeline 12, i.e. the shaded sectional area with position 12. No material flow takes place between the inner wall 16 and the wall of the second/third pipeline 14, 15. The second liquid phase flows inside the second pipeline 14. The third liquid phase flows inside the third pipeline 15.

Figure 2B:
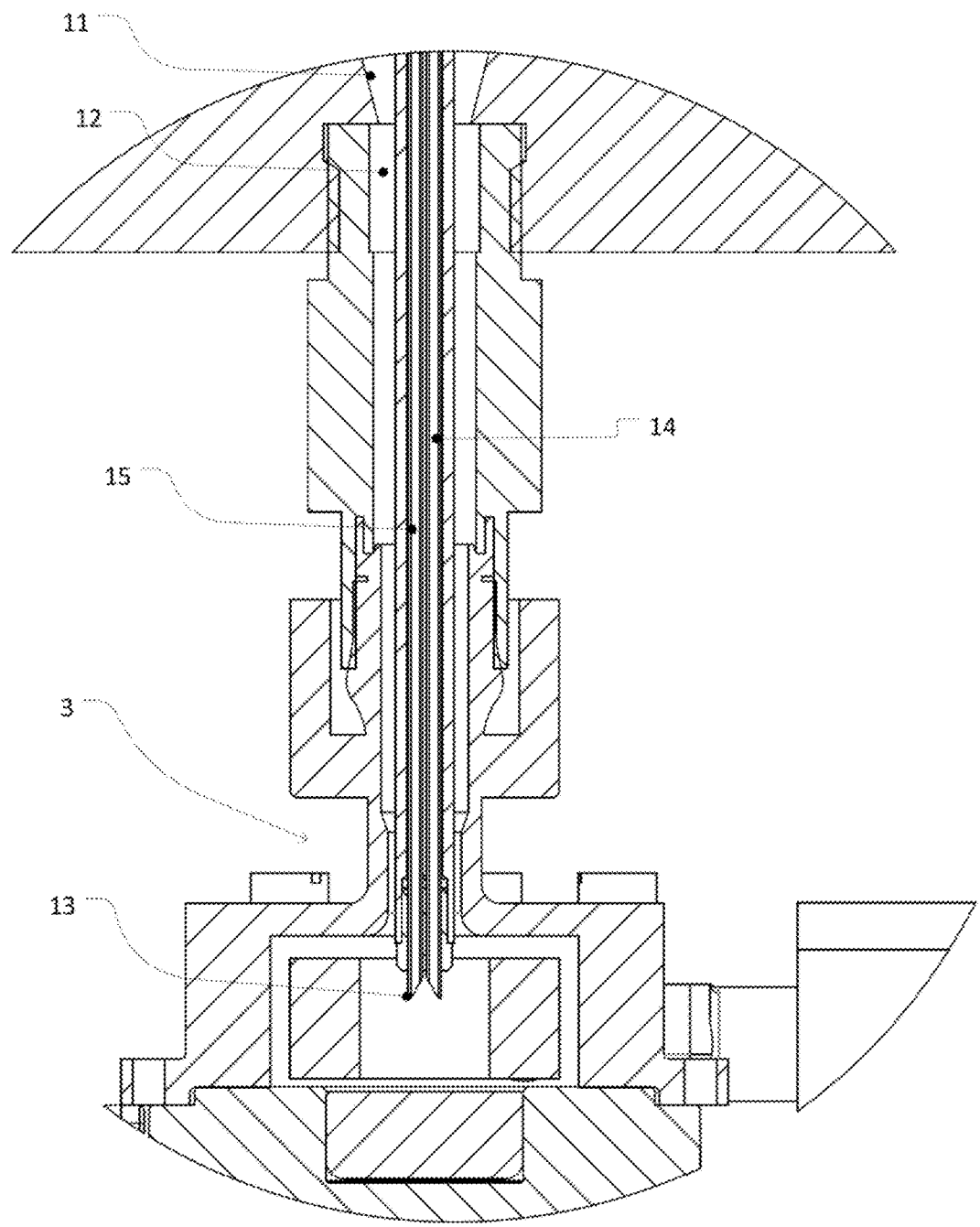
FIG. 2B: shows a second variant of an apparatus according to the invention, showing the active element and feeds in detail.
Figure 2C:
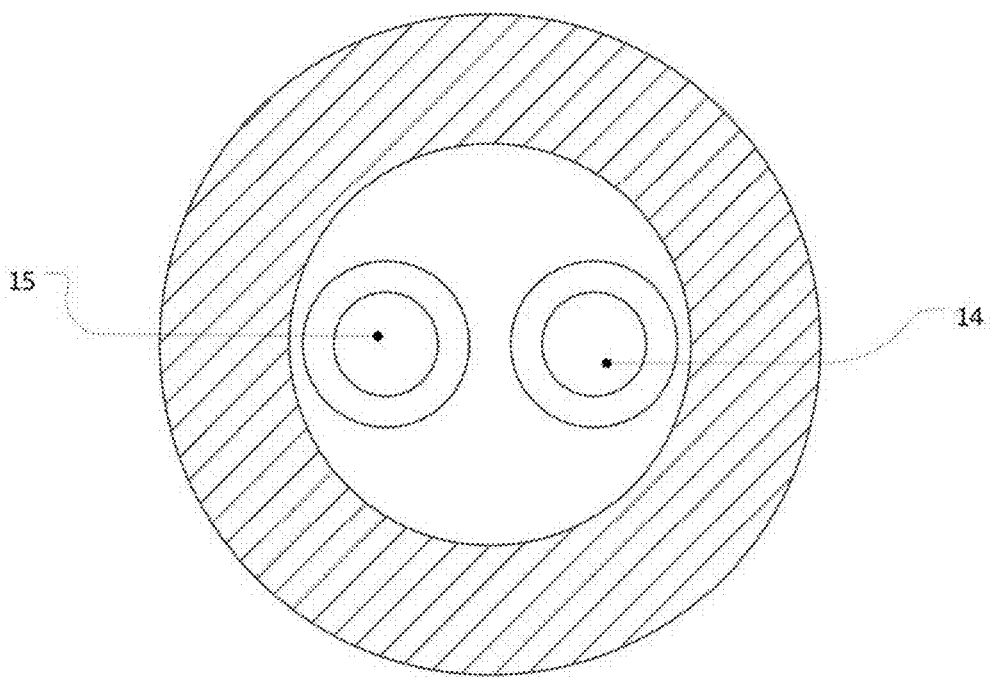
FIG. 2C: shows a second variant of an apparatus according to the invention, section through the feeds
Figure 5A:
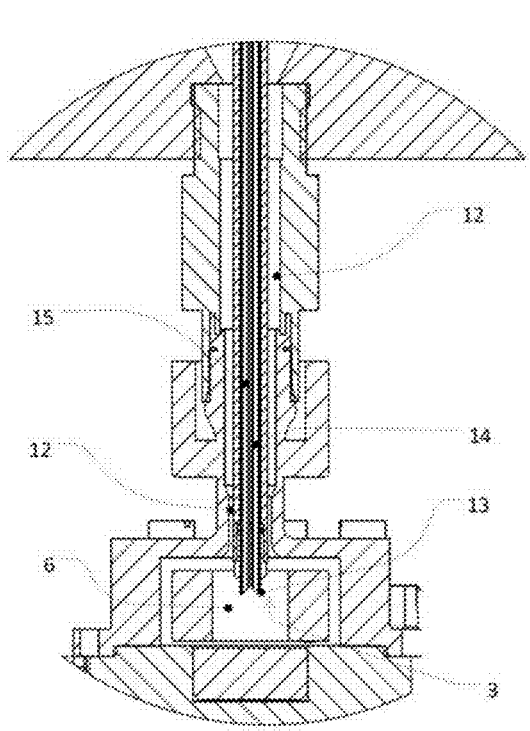
FIG. 5A: shows the active element in a first axial position.
Figure 5B:
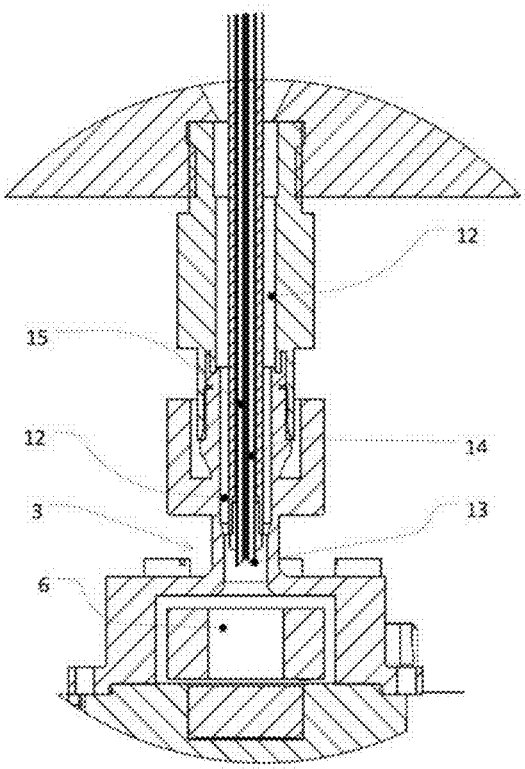
FIG. 5B: shows the active element in a second axial position.

FIGS. 5A and 5B show how in the tertiary apparatuses shown in FIGS. 2A and 3 the second pipeline 14 together with the third pipeline 15 may be axially displaced relative to the first pipeline 12. In FIG. 5B the vertical distance between the opening with the ground end 13 and the pump 6 is greater than in FIG. 5A where the opening projects into the pump 6. This is accomplished with a linear drive not shown here. The first pipeline 12 remains unmoved. The parallel nature and vertical orientation of all pipelines 12, 14, 15 is always retained.

It is also conceivable to make the second pipeline 14 and the third pipeline 15 axially movable separately from one another. This is not possible in the embodiments shown here; the second pipeline 14 and the third pipeline 15 can only be moved as a package. It is also possible to make the first pipeline 12 axially movable as an alternative to moving the second and/or third pipeline. This is because the decisive factor is the relative axial orientation of the pipelines and not the absolute position. However, in the embodiments shown here the first pipeline 12 is fixed.

By varying the axial orientation of the two pipelines 12, 14 to one another the flow conditions in the active element 3 are varied and the formation of the nanocarriers/the nanoformulation thus optimized.

Figure 6:
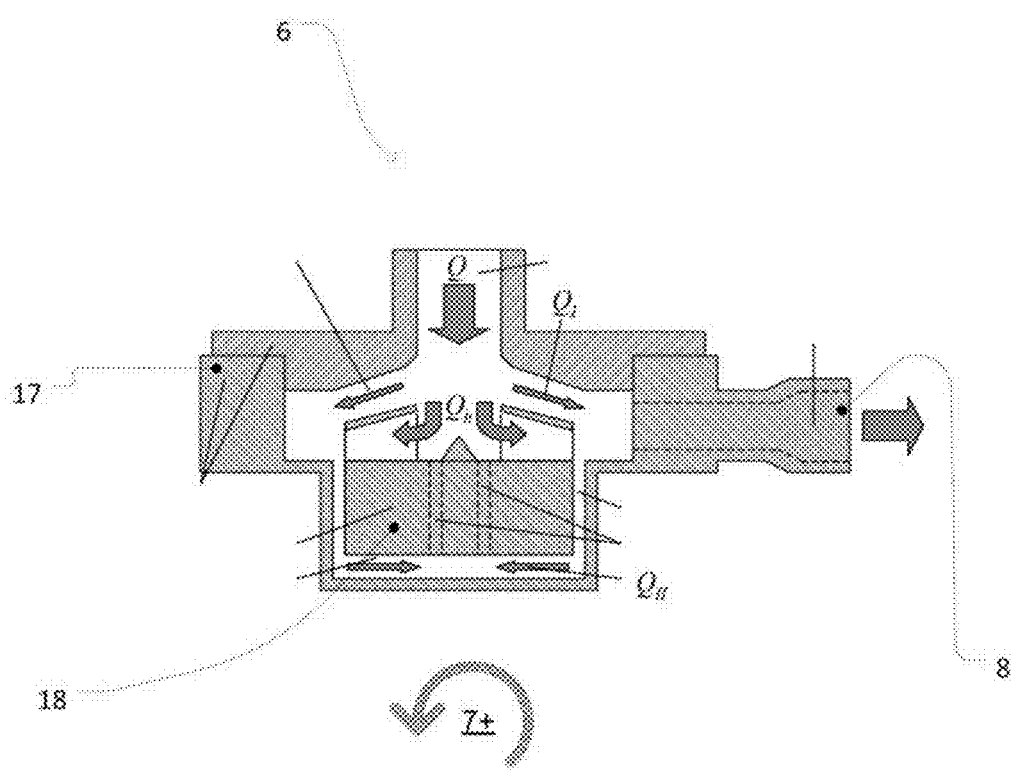
FIG. 6: shows a schematic diagram of a levitronic pump.

FIG. 6 is a schematic diagram of the pump 6. The pump 6 is in the form of a centrifugal pump. It comprises an immovable housing 17 in which a rotor 18 is rotatably mounted. The rotor 18 may also be referred to as an impeller. The propulsion and mounting of the rotor 18 is effected via a rotating field 7*. The rotational axis of the rotor 18 is vertically oriented. It is preferable when the rotational axis is coaxial with the axis of the first pipeline 12. This is the case in the variants shown in FIGS. 1, 2 and 3.

One feature of the pump 6 is that it is a levitronic pump. This means that the rotor 18 is coupled to the propulsion means 7 not via a rigid shaft but rather magnetically via the rotating field 7*. The surrounding rotating field 7* rotates the rotor 18. This allows the rotor 18 to be contactlessly mounted and set into rotary motion around its vertical rotational axis.

In operation the mixture enters the housing 17 of the pump 6 from above. The mixture is accelerated radially outwards in a horizontal plane by the rotating rotor 18 and exits the housing 16 again via the discharge 8. A portion of the mixture flows around the rotor 18 on its underside. This is possible on account of the magnetic mounting and force transmission.

Figure 7A:
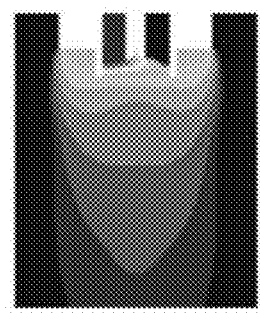
FIG. 7A: shows a flow simulation, first sectional view.
Figure 7A:
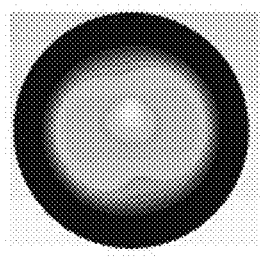
Figure 7B:
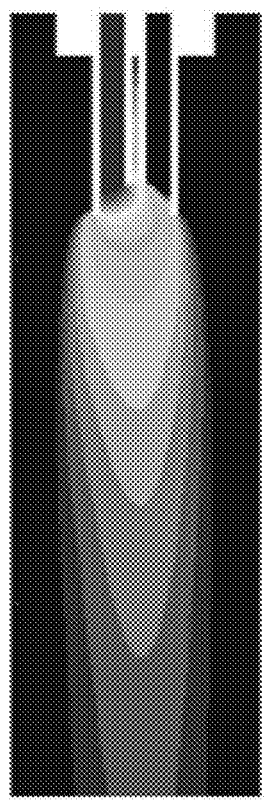
FIG. 7B: shows a flow simulation, second sectional view.
Figure 7B:
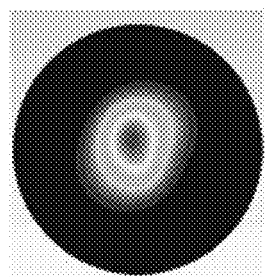
Figure 7C:
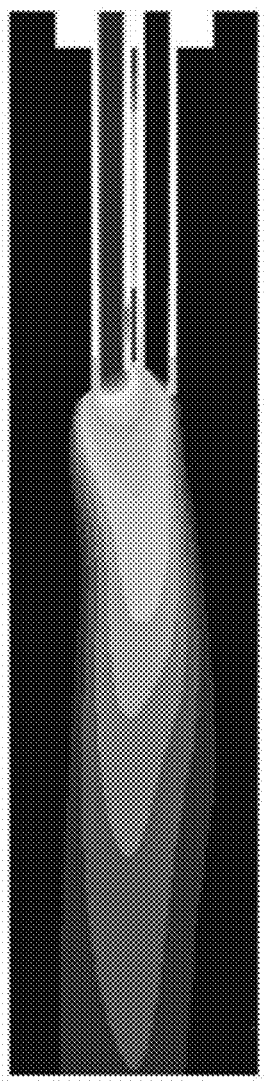
FIG. 7C: shows a flow simulation, third sectional view.
Figure 7C:
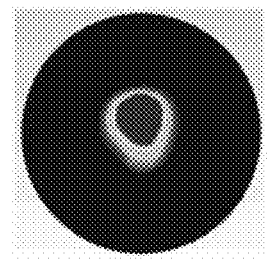

FIGS. 7A, 7B, and 7C show a flow simulation through an active element 3 of the apparatus shown in FIG. 3. The figure shows the local concentration of ethanol supplied via the left hand capillary. The "ethanol concentration" varies in all three spatial directions according to the capillary length outside the lance. The three sectional views show the cross section in each case about 2 mm beyond the end of the capillaries. The first sectional view in FIG. 7A shows that even after a path length of only about 2 mm only a 1 mol percent concentration difference of ethanol relative to the main flow is detectable. The second sectional view (capillary length 10 mm) shown in FIG. 7B shows after 2 mm an elongate core flow where the concentration difference is about 6 mol percent. The third sectional view (capillary length 20 mm) shown in FIG. 7C shows after 2 mm an elongate core flow where the concentration difference is about 10 mol percent.

Figure 8:
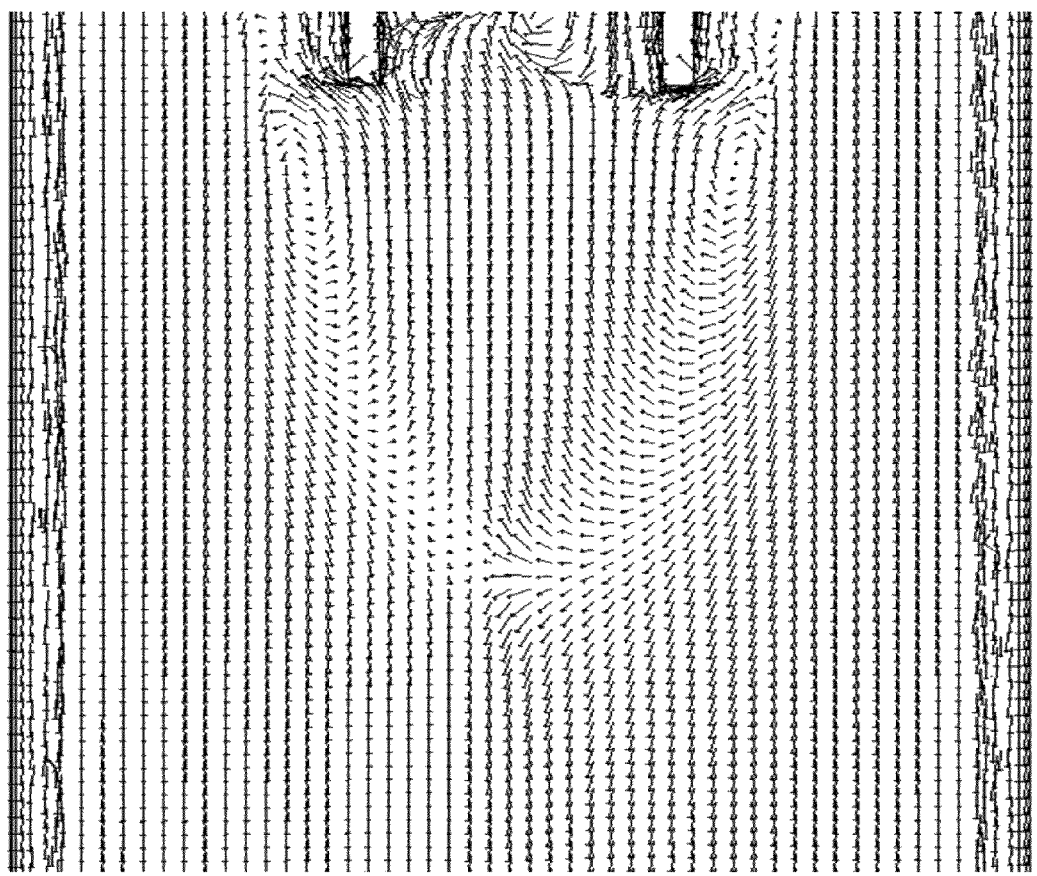
FIG. 8: shows a flow vector image.

FIG. 8 shows a flow vector image of an apparatus having two 3 mm capillaries in the region of the active element. The velocity vectors of the liquid flow are represented therein as small arrows. It is apparent to those skilled in the art that the flow paths of the first liquid phase (outside) remain largely parallel/vertical. Only in the region of the feed for the second/third liquid phase (central) via the two capillaries is there a homogenous deviation of the flow direction, though this cannot be described as turbulent.

EXAMPLES

The processes according to the invention will now be more particularly elucidated with reference to experimental examples. Table 0 contains an overview of the examples.

All experiments were carried out with an apparatus corresponding to FIGS. 2A/3. The internal volume of the reservoir 1 was varied by moving the insert 111. The apparatus comprised a levitronic pump from Levitronix. Metered addition apparatuses were additionally employed for metered addition of the first and second liquid phase. These are not shown in the drawings.

A Zetasizer instrument from Malvern Panalytical Ltd, GB was used to determine polydispersity (PDI) and average particle size (Zav). The backscattering angle was set to 173°.

TABLE 0

Overview of examples

| | | First liquid phase | | | Second liquid phase | | | | Third liquid phase | |
|---|---|---|---|---|---|---|---|---|---|---|
| Example Group | no. | Dispersion medium | Buffer | Active ingredient | Dispersion medium | Buffer | Nanocarrier precursor | Active ingredient | Dispersion medium | Nanocarrier/ active ingredient precursor |
| 1 | I | Water | Ammonium sulphate | n/a | Ethanol | n/a | EPC chol | n/a | n/a | n/a |
| 1 | II | Water | Ammonium sulphate | n/a | Ethanol | n/a | EPC chol | n/a | n/a | n/a |
| 1 | III | Water | Ammonium sulphate | n/a | Ethanol | n/a | EPC chol | n/a | n/a | n/a |
| 2 | IV | Water | n/a | n/a | Ethanol | n/a | NAT 8539 | n/a | n/a | n/a |
| 2 | V | Water | n/a | n/a | Ethanol | n/a | NAT 8539 | n/a | n/a | n/a |
| 3 | VI | Water | PVA | n/a | Acetonitrile | n/a | PLGA | Ritonavir | n/a | n/a |
| 4 | VII | Water | Phosphate | n/a | Water | Acetate | Poly A | Poly A | Ethanol | DODMA, DSPC, Cholesterol, PEG-DMG |
| 4 | VIII | Water | Phosphate | n/a | Water | Acetate | Poly A | Poly A | Ethanol | DODMA, DSPC, Cholesterol, PEG-DMG |
| 5 | IX | Water | n/a | n/a | Water | Acetate | PEI | n/a | Water | Poly A |
| 5 | X | Water | n/a | Poly A | Water | Acetate | PEI | n/a | n/a | n/a |
| 6 | XI | Water | n/a | n/a | Ethanol/DMSO | n/a | RESOMER® RP d 155 | n/a | n/a | n/a |
| 6 | XII | Water | n/a | n/a | Ethanol/DMSO | n/a | RESOMER® RP d 255 | n/a | n/a | n/a |
| 6 | XIII | Water | n/a | n/a | Ethanol/DMSO | n/a | RESOMER® RP d 505 | n/a | n/a | n/a |
| 7 | XIV | Water | n/a | n/a | Ethyl acetate | n/a | PLGA | Meloxicam (in DMSO) | PVA | n/a |

Legend for table 0:
PVA = polyvinyl alcohol
EPC Chol = lipoid E PC and cholesterol HP
NAT 8539 = soy phosphatidylcholine
PLGA = poly(D,L-lactide-co-glycolide)
Poly A = polyadenosine monophosphate
DODMA = 1,2-dioleyloxy-3-dimethylaminopropane
DSPC = distearoylphosphatidylcholine
PEG-DMG = polyethylene glycol dimethacrylate
PEI = polyethyleneimine Example Series 1: Production of Liposomes as Nanocarriers for Pharma Applications As shown in examples I to III the levitronic pump allows generation of liposomes over a wide concentration range of lipids with a robust process. Lipoid E PC and cholesterol HP in the ratio (55 mol %:45 mol %) were used here in varying concentrations as an example formulation.

Example I

In example I 700 mL of a 250 mM ammonium sulfate buffer was initially charged as first liquid phase and 77.5 mL of second liquid phase comprising 200 mg/ml of EPC-chol in ethanol were metered in. The stationary volume flow of the first liquid phase was around 8 liters per minute, into which 10 ml per minute of second liquid phase were then added over a period of around 8 minutes. The metered addition was carried out using a rigid hose or a capillary above the levitronic pump. A liposome dispersion having an average particle size of about 150 nm was produced. The result was also reproducible at half the metered addition rate and a batch size reduced to 183.2 ml. This demonstrates that the apparatus allows good upscaling. Results are reported in table 1.

Example II

In example II the lipid concentration in the organic phase and thus also in the product was doubled while retaining the same EPC-chol lipid ratio (55 mol %:45 mol %). At comparable process parameters to those in example I the resulting particles are larger and have a higher polydispersity. This example further investigated the effect of pump speed/stationary volume flow of the first liquid phase. It was shown that for this formulation higher pump rates give better results. Results are reported in table 2.

Example III

In example III the lipid concentration in the organic phase and thus also in the product was reduced while retaining the same EPC-chol lipid ratio (55 mol %:45 mol %). The lipid content and the organic phase was 15.2 mg/ml and the ratio of aqueous phase to organic phase was varied while the effect of pump speed/stationary volume flow of the first liquid phase was once again investigated. A second capillary of reduced internal diameter was also employed. The results reflect a robust process with results between 79.85 nm and 108.4 nm. The lowest particle size was achieved with a fine capillary for metered addition of the organic phase. Results are reported in table 3.

Example Series 2: Liposomal Carrier Systems for Cosmetic Applications

Phospholipids are important constituents of the cell membranes and thus naturally occurring. They may be used as components of liposomes as carriers for low-solubility cosmetically active substances such as for example Vitamin A & E or Coenzyme Q10 and improve skin penetration. These properties of the liposomes are finding increasing application in cosmetics as well as the formulation of pharmaceuticals. The liposomes containing phospholipids also have intrinsic biological activities, and this is of great importance for the normal functioning of the skin. Accordingly, "empty" liposomes without any contents have their place as moisturizers in cosmetics.

As shown in examples IV and V the levitronic pump may be used to process phospholipids of a cosmetic standard formulation into liposomes. NAT 8539 (purified soy phosphatidylcholine in ethanol) was employed here in varying concentration as an example formulation.

Example IV

In example IV successful production of liposomes was achieved by initially charging 583 g of water as first liquid phase, followed by metered addition of 212 g of second liquid phase consisting of 107 g of NAT 8539 (ethanolic solution) and 105 g ethanol. The metered addition was carried out using a capillary above the levitronic pump. The results of various arrangements are shown in the table which follows. A higher rate of metered addition tends to result in smaller particles. Higher flow rates (rpm) result in smaller particle sizes and narrower particle size distribution. The effect of the distance between the capillary and the pump head is a parameter that may be neglected. The results are shown in table 4.

Example V

In example V successful production of liposomes was achieved by initially charging 583 g of water as first liquid phase, followed by metered addition of 212 g of second liquid phase consisting of 53.5 g of NAT 8539 (ethanolic solution) and 158.5 g ethanol. The lipid concentration in the organic phase and thus also in the product was thus halved. The metered addition was carried out using a capillary above the levitronic pump. The resulting particles are <200 nm and have a PDI below 0.2. The results are shown in table 5.

Example Series 3: Biodegradable Nanoparticles as Pharmaceutical Carrier Systems for Pharmaceutical Applications Poly(D,L-lactide-co-glycolide) (PLGA) is an established biodegradable polymer for producing nanoparticles which biodegrade in an aqueous environment over controllable time periods to allow release of an active pharmaceutical ingredient. An example formulated in this way which is very successful on the market is Eligard®, an effective therapy for treatment of symptoms occurring due to prostate cancer. The active ingredient is Leuprolid (a testosterone inhibitor) embedded in PLGA nanoparticles for subcutaneous injection.

Example VI

As shown in example VI the levitronic pump allows PLGA-based nanoparticles to be produced over a wide concentration range with a robust process with or without active ingredient loading. RESOMER® RG 502 H, a poly(D,L-lactide-co-glycolide), obtainable from Evonik was employed as an example formulation in a varying mixture ratio to the aqueous phase (2% polyvinyl alcohol (PVA) solution). The PVA solution was initially charged as first liquid phase and circulated at varying rates (pump speeds) and the organic PLGA solution in acetonitrile was metered in at varying rates as a second liquid phase. To this end, RG 502 H was first completely dissolved in acetonitrile with stirring. The concentration of the PLGA in the organic phase was 10 mg/ml.

The PLGA nanoparticles were also successfully loaded with a model active ingredient having poor solubility in water, namely Ritonavir which is approved for treatment of HIV. In the *verum* experiments 10% or 20% of Ritonavir based on the PLGA were additionally added.

The resulting particles are suitable in terms of size for sterile filtration and have a narrow particle size distribution which is indicative of quality. It was demonstrated that "downstream processing" by tangential flow filtration (TFF) to remove unencapsulated active ingredient and residual solvent and freeze-drying to achieve a required shelflife, as required for pharmaceutical production, may be carried out successfully. The obtained particles have an encapsulation efficiency of up to 14.59% and are successfully redispersible after freeze-drying to achieve similar particle sizes and particles size distributions as immediately after the production process.

The results are shown in table 6.

Example Series 4: Lipid Nanoparticles as Pharmaceutical Carrier Systems for Pharmaceutical Applications, Primarily mRNA Since the approval of a first preparation based on lipid nanoparticles (Onpattro®) by the FDA in 2018 there has been increasing interest in this formulation strategy. LNPs are today also used for formulation of mRNA as active constituents. This combines the advantages of nanoparticulate formulations generally (mechanical protection of the active ingredient, longer residence time in the organism, preferential uptake in tumor tissue (EPR effect)) with specific effects brought about by the physicochemical properties of the employed lipid. Accordingly, the chemically unstable and charged mRNA may be transported through the cell membrane with a lipid nanoparticle, where at low pH ionizable lipids ensure that the mRNA discharge cargo and the information present in the mRNA can later be translated into proteins.

Example VII

As shown in example VII the levitronic pump allows lipid nanoparticles to be produced with a robust process with polyadenosine monophosphate (poly A) as a surrogate for mRNA.

A formulation containing DODMA (50 mol %) as an ionizable lipid and DSPC, cholesterol and PEG-DMG (10/38.5/1.5 mol %) as further constituents of the lipid fraction at a combined lipid concentration of 15 mM was used as an example formulation. The volume of the lipid phase was 20 ml. The N/P ratio was 3:1 in the example formulation. The poly A was dissolved in 60 ml of a 5 mM acetate buffer at pH 4.0.

70 mL of a phosphate buffer pH 7.4 USP were added to the reservoir vessel and circulated with the levitronic pump at 10 000 rpm. Simultaneously, the poly A-containing acetate buffer was injected at 15 ml/min and the lipid solution at 5 ml/min using two capillaries. Upon impacting of the solutions in the region of the capillary outlet (see diagram) lipid nanoparticles were formed at pH 4 and these were immediately contacted with the phosphate buffer due the volume flow of the levitronic pump and, as a result of its higher buffer capacity, adjusted to pH 7 and thus stabilized.

Results obtained by gel electrophoresis (E-Gel® EX invitrogen Agarose 1%) show that the poly A was successfully bound in the lipid nanoparticles, remained in the injection well of the gel and produced a strong signal while free Poly A ran into the gel and showed a typical distribution.

The results are shown in table 7.

Example VIII

A formulation containing DODMA (50 mol %) as an ionizable lipid and DSPC, cholesterol and PEG-DMG (10/38.5/1.5 mol %) as further constituents of the lipid fraction at a combined lipid concentration of 15 mM was used as an example formulation. The volume of the lipid phase was 37.5 ml. The N/P ratio was 3:1 in the example formulation. The poly A was dissolved in 112.5 ml of a 5 nnM acetate buffer at pH 4.0 and added to the reservoir vessel and circulated with the levitronic pump at 14 000 rpm. Simultaneously, the lipid solution was injected at 5 ml/min using a capillary. Upon impacting of the solutions in the region of the capillary outlet lipid nanoparticles were formed at pH 4. The particle solution was withdrawn from the apparatus and externally adjusted to pH 7 by addition of phosphate buffer pH 7.4 USP to stabilize the particles.

The results are shown in table 8.

Example Series 5: Polyplexes as Pharmaceutical Carrier Systems for Pharmaceutical Applications, Primarily mRNA Similarly to the lipid nanoparticles (LNPs) it is also possible to use polyplexes, for example composed of polyethyleneimine and (m)RNA or DNA, to bring these substances to their intracellular site of action by non-viral delivery. Polyplexes can markedly increase the stability of the active constituents. The formation of the polyplexes is a consequence of charge differences between the polyethyleneimine which is cationic in slightly acidic solution and the anionic phosphate residues of the (m)RNA or DNA.

Example IX 80 mL of RNase-free water were initially charged in the reservoir of the apparatus and circulated at 10 000 rpm (first liquid phase). 33.5 mL of a 100 µg/ml poly A solution in RNase-free water were produced with stirring and serve as third liquid phase. This phase was injected via a capillary at 5 ml/min. 2.944 ml of a stock solution consisting of 10 g/l of polyethyleneimine are mixed with 3 mL of a 1M acetate buffer and 29.056 ml of water (second liquid phase). The resulting N/P ratio is 15. This mixture is injected at 5 ml/min via a further capillary.

The results are shown in table 9.

Example X

In example X identical amounts of poly A and polyethyleneimine as in example IX were employed but in this example the poly A solution was introduced into the first reservoir diluted in a greater volume (115 ml) and circulated at 10 000 rpm. The polyethyleneimine solution previously described in example IX (35 mL) is injected at 5 ml/min via a capillary.

The results are shown in table 10.

From a combination of the examples IX and X those skilled in the art will recognize the good scalability of the process operated with the apparatus, since in example X poly A was metered in via the first liquid phase in a much lower concentration than in example IX where poly A was introduced via the third phase.

Example Series 6: Polymeric Micelles as Pharmaceutical Carrier Systems for Pharmaceutical Applications Polymeric micelles can be used as pharmaceutical carrier systems, in which the systemic circulation prolonging effect of polyethylene glycol (PEG) on the outer surface of the structure is combined with the ability of polylactic acid (PLA) to load (lipophilic) active components within the micellar structure. Example XI to XIII show polymeric micelles formulations in the nanometer size range produced by the herein described mixing process.

Example XI 180 mL of deionized water were initially charged in the reservoir of the apparatus and circulated at 3 000 rpm (first liquid phase). 16 mL of a stock solution consisting of 6.2% RESOMER® RP d 155, 55.8% ethanol, 38.0% DMSO served as organic phase (second liquid phase). This mixture is injected at 10 ml/min via a capillary. RESOMER® RP d 155 is a mPEG-PLA Diblock copolymers containing a 5 kDa mPEG block and 15 wt % PEG.

The results are shown in table 11.

Example XII 180 mL of deionized water were initially charged in the reservoir of the apparatus and circulated at 3 000 rpm (first liquid phase). 16 mL of a stock solution consisting of 5.7% RESOMER® RP d 255, 51.3% ethanol, 43.0% DMSO served as organic phase (second liquid phase). This mixture is injected at 10 ml/min via a capillary. RESOMER® RP d 255 is a mPEG-PLA Diblock copolymers containing a kDa mPEG block and 25 wt % PEG.

The results are shown in table 12.

Example XIII 180 mL of deionized water were initially charged in the reservoir of the apparatus and circulated at 3 000 rpm (first liquid phase). 16 mL of a stock solution consisting of 7% RESOMER® RP d 505, 62.6% ethanol, 30.4% DMSO served as organic phase (second liquid phase). This mixture is injected at 10 ml/min via a capillary. RESOMER® RP d 505 is a mPEG-PLA Diblock copolymers containing a 5 kDa mPEG block and 50 wt % PEG The results are shown in table 13.

Example Series 7: Biodegradable Microparticles as Pharmaceutical Carrier Systems for Pharmaceutical Applications As shown in example series 3 the levitronic mixing allows PLGA-based nanoparticles to be produced over a wide concentration range with a robust process with or without active ingredient loading. By process parameter- and excipient modification the herein described process can also be used to generate polymeric microparticles. There are examples for successfully marketed polymeric microparticles such as Bydureon® (AstraZeneca). Particles in the size range between 20 µm and 90 µm can be achieved by the herein described process. Such particles are considered as microcarrier.

RESOMER® RG 502 H, a poly(D,L-lactide-co-glycolide), obtainable from Evonik, was employed as an example formulation. Deionized water was initially charged as first liquid phase and circulated at varying rates (pump speeds) and the organic PLGA solution was metered in at varying rates as a second liquid phase (dispersed phase/DP). To this end, RG 502 H was first completely dissolved in ethyl acetate with stirring. The concentration of the PLGA in the organic phase was varied between and 30%. As a third liquid phase (continuous phase/CP) a 2% PVA solution was added via the second capillary. The CP/DP ratio was varied between 1:1 and 1:5.

In addition to placebo formulations, the PLGA microparticles were also successfully loaded with a model active ingredient, namely Meloxicam which is approved as a non-steroidal anti-inflammatory drug. In the *verum* experiments Meloxicam was dissolved at 5% in DMSO and added to the organic phase at 10% and 20% based on the PLGA mass.

The resulting particles were filtered through a 20 µm sieve and resuspended in water. The microparticles are suitable in terms of size and have a narrow particle size span which is indicative of quality. The obtained meloxicam microparticles have an encapsulation efficiency between 92.7% (10% Drugload) and 96.6% (20% Drugload). Deviating to all other examples, size determination of polymeric microparticles was conducted at a MasterSizer system (Malvern Panalytical)

The results are shown in table 14.

TABLE 1

| | | Example I results | | | | | |
|---|---|---|---|---|---|---|---|
| Experiment number | Total lipids concentration (EPC-COL) in EtOH | Total volume in system [ml] | Pump speed [rpm] | Addition rate [ml/min] | Sampling time [min] (after completed addition) | Zav (backscattering) | PDI |
| 21836/21 | 200 mg/ml | 777.5 ml (700 ml ammonium sulfate + 77.5 ml EPC-col in EtOH) | 14000 | 10 ml/min | 10 | 153.2 | 0.309 |
| | | | | | 40 | 150.0 | 0.254 |
| | | | | | 70 | 147.5 | 0.246 |
| | | | | | 100 | 144.3 | 0.253 |
| 21836/29_2 | 200 mg/ml | 183.2 ml (150 ml ammonium sulfate + 33.2 ml EPC-col in EtOH) | 14000 | 5 ml/min | 5 | 155.6 | 0.216 |
| | | | | | 30 | 156.2 | 0.219 |
| | | | | | | 156.8 | 0.233 |
| | | | | | | 156.0 | 0.239 |

TABLE 2

Example II results

| Experiment number | Total lipids concentration (EPC-COL) in EtOH | Total volume in system [ml] | Pump speed [rpm] | Sampling time [min] (after completed addition) | Zav (backscattering) | PDI |
| --- | --- | --- | --- | --- | --- | --- |
| 21836/20 | 400 mg/ml | 500 ml (450 ml ammonium sulfate + 50 ml EPC-col in EtOH) | 10000 | 10<br>90 | 549.9<br>512.4 | 0.705<br>0.708 |
| 21836/24 | 400 mg/ml | 777.5 ml (700 ml ammonium sulfate + 77.5 ml EPC-col in EtOH) | 14000 | 30 | 422.4<br>398.5 | 0.710<br>0.785 |
| 21836/26 | 400 mg/ml | 777.5 ml (700 ml ammonium sulfate + 77.5 ml EPC-col in EtOH) | 8200 | 30 | 1001<br>973.1 | 0.582<br>0.838 |

TABLE 3

Example III results

| Experiment number | Total lipids concentration (EPC-COL) in EtOH | Ratio aqueous phase:organic phase | Total volume in system [ml] | Pump speed [rpm] | Addition rate of organic solution [ml/min] | Capillary type/ distance to pump | Zav (backscattering) | PDI |
| --- | --- | --- | --- | --- | --- | --- | --- | --- |
| 21836/33_1 | 15.2 mg/ml | 3:1 | 160 ml [120 ml aqueous phase/40 ml organic phase] | 14000 | 10 ml/min | Pipe ext diameter 3.25 mm/20 mm | 108.4<br>106.5 | 0.136<br>0.097 |
| 21836/33_2 | 15.2 mg/ml | 6:1 | 141 ml [120 ml aqueous phase/21 ml organic phase] | 14000 | 10 ml/min | Pipe ext diameter 3.25 mm/20 mm | 92.67<br>91.53 | 0.144<br>0.113 |
| 21836/33_3 | 15.2 mg/ml | 9:1 | 150 ml [135 ml aqueous phase/15 ml organic phase] | 14000 | 10 ml/min | Pipe ext diameter 3.25 mm/20 mm | 92.81<br>88.88 | 0.129<br>0.159 |
| 21836/33_4 | 15.2 mg/ml | 9:1 | 150 ml [135 ml aqueous phase/15 ml organic phase] | 5000 | 10 ml/min | Pipe ext diameter 3.25 mm/20 mm | 90.75<br>89.37 | 0.134<br>0.110 |
| 21836/33_5 | 15.2 mg/ml | 9:1 | 150 ml [135 ml aqueous phase/15 ml organic phase] | 14000 | 10 ml/min | Fine capillary/ 20 mm | 81.12<br>80.78 | 0.160<br>0.175 |
| 21836/33_6 | 15.2 mg/ml | 9:1 | 150 ml [135 ml aqueous phase/15 ml organic phase] | 14000 | 5 ml/min | Fine capillary/ 20 mm | 81.56<br>79.85 | 0.202<br>0.188 |

TABLE 4

Example IV results

| Experiment number | Total lipids concentration (EPC-COL) in EtOH | Total volume in system [g] | Pump speed [rpm] | Addition rate of organic solution [ml/min] | Capillary distance to pump | Zav (backscattering) | PDI |
| --- | --- | --- | --- | --- | --- | --- | --- |
| 21836/30_1 | 386.90 mg/ml [38.69%] | 795 g [582.56 g aqueous phase/ 212.24 g organic phase] | 14000 | 5 ml/min | 20 mm | 238.3 | 0.216 |
| 21836/30_2 | 386.90 mg/ml [38.69%] | 795 g [582.56 g aqueous phase/ 212.24 g organic phase] | 14000 | 15 ml/min | 20 mm | 235.5 | 0.146 |

TABLE 4-continued

Example IV results

| Experiment number | Total lipids concentration (EPC-COL) in EtOH | Total volume in system [g] | Pump speed [rpm] | Addition rate of organic solution [ml/min] | Capillary distance to pump | Zav (backscattering) | PDI |
|---|---|---|---|---|---|---|---|
| 21836/30_3 | 386.90 mg/ml [38.69%] | 795 g [582.56 g aqueous phase/ 212.24 g organic phase] | 14000 | 25 ml/min | 20 mm | 224.7 | 0.173 |
| 21836/30_4 | 386.90 mg/ml [38.69%] | 795 g [582.56 g aqueous phase/ 212.24 g organic phase] | 14000 | 35 ml/min | 20 mm | 217.6 | 0.157 |
| 21836/30_5 | 386.90 mg/ml [38.69%] | 795 g [582.56 g aqueous phase/ 212.24 g organic phase] | 5000 | 15 ml/min | 20 mm | 314.4 | 0.286 |
| 21836/30_6 | 386.90 mg/ml [38.69%] | 795 g [582.56 g aqueous phase/ 212.24 g organic phase] | 10000 | 15 ml/min | 20 mm | 267.7 | 0.156 |
| 21836/30_7 | 386.90 mg/ml [38.69%] | 795 g [582.56 g aqueous phase/ 212.24 g organic phase] | 14000 | 15 ml/min | 20 mm | 234.9 | 0.125 |
| 21836/30_8 | 386.90 mg/ml [38.69%] | 795 g [582.56 g aqueous phase/ 212.24 g organic phase] | 14000 + 90 min recirculation after completed addition | 15 ml/min | 20 mm | 216.3 | 0.156 |
| 21836/30_9 | 386.90 mg/ml [38.69%] | 795 g [582.56 g aqueous phase/ 212.24 g organic phase] | 14000 | 15 ml/min | 10 mm | 238.6 | 0.232 |
| 21836/30_10 | 386.90 mg/ml [38.69%] | 795 g [582.56 g aqueous phase/ 212.24 g organic phase] | 14000 | 15 ml/min | 20 mm | 237.7 | 0.138 |
| 21836/30_11 | 386.90 mg/ml [38.69%] | 795 g [582.56 g aqueous phase/ 212.24 g organic phase] | 14000 | 15 ml/min | 30 mm | 230.7 | 0.174 |

TABLE 5

Example V results

| Experiment number | Total lipids concentration (EPC-COL) in EtOH | Total volume in system [g] | Pump speed [rpm] | Addition rate of organic solution [ml/min] | Capillary distance to pump | Zav (backscattering) | PDI |
|---|---|---|---|---|---|---|---|
| 21836/30_12 | 193.45 mg/ml [19.35%] | 795 g [582.56 g aqueous phase/ 212.24 g organic phase] | 14000 | 15 ml/min | 20 mm | 197.9 | 0.126 |

TABLE 6

Example VI results

| Experiment number | Organic phase | Vessel/ batch size | Capillary | Pump speed [rpm] | Rate of addition [ml/min] | Zav (backscattering) | PDI |
|---|---|---|---|---|---|---|---|
| 21836/30 | ACN/10 mg/ml/ 77.8 ml | Steel tank/777.8 ml after addition of org. phase | Wide (3.25 mm ext diameter) | 14000 | 10 ml/min | 101.3 100.2 | 0.200 0.197 |

TABLE 6-continued

Example VI results

| Experiment number | Organic phase | Vessel/ batch size | Capillary | Pump speed [rpm] | Rate of addition [ml/min] | Zav (backscattering) | PDI |
|---|---|---|---|---|---|---|---|
| 21836/31_1 | ACN/10 mg/ml/ 15 ml | Plexiglas tank/ 150 ml after addition of org. phase | fine | 14000 | 5 ml/min | 117.6 116.6 | 0.199 0.202 |
| 21836/31_2 | ACN/10 mg/ml/ 15 ml | Plexiglas tank/ 150 ml after addition of org. phase | Wide (3.25 mm ext diameter) | 10000 | 10 ml/min | 88.43 87.77 | 0.213 0.202 |
| 21836/31_3 | ACN/10 mg/ml/ 15 ml | Plexiglas tank/ 150 ml after addition of org. phase | Wide (3.25 mm ext diameter) | 5000 | 10 ml/min | 106.0 105.2 | 0.164 0.170 |
| 21836/31_4 | ACN/10 mg/ml/ 15 ml | Plexiglas tank/ 150 ml after addition of org. phase | Wide (3.25 mm ext diameter) | 2500 | 10 ml/min | 99.70 98.41 | 0.214 0.204 |
| 21836/32_1 | ACN/10 mg/ml/ 15 ml | Plexiglas tank/ 150 ml after addition of org. phase | Wide (3.25 mm ext diameter) | 7500 | 10 ml/min | 92.83 91.79 | 0.194 0.160 |
| 21836/32_2 | ACN/10 mg/ml/ 15 ml | Plexiglas tank/ 150 ml after addition of org. phase | Wide (3.25 mm ext diameter) | 10000 | Bolus (15 ml in 15 sec) | 102.6 102.1 | 0.205 0.197 |
| 21836/32_3 | ACN/10 mg/ml/ 15 ml | Plexiglas tank/ 150 ml after addition of org. phase | Wide (3.25 mm ext diameter) | 10000 | Slow (2.5 ml/min) | 105.4 103.7 | 0.170 0.177 |
| 1836/34_1 | ACN/10 mg/ml/ 15 ml + 1% Ritonavir | Plexiglas tank/ 150 ml after addition of org. phase | Wide (3.25 mm ext diameter) | 10000 | 10 ml/min | 98.06 96.94 | 0.251 0.239 |
| 1836/34_1 | ACN/10 mg/ml/ 15 ml + 2% Ritonavir | Plexiglas tank/ 150 ml after addition of org. phase | Wide (3.25 mm ext diameter) | 10000 | 10 ml/min | 102.0 98.06 | 0.272 0.199 |

TABLE 7

Example VII results

| Experiment number | Total lipids concentration in EtOH | Total volume in system [g] | Pump speed [rpm] | Addition rate of organic solution [ml/min] | Capillary type/distance to pump | Zav (backscattering) | PDI |
|---|---|---|---|---|---|---|---|
| 21836/36_1 | 15 mM (thereof 7.5 mM DODMA) | 150 ml 70 ml phosphate buffer pH 7.4 initially as outer phase in levitronic pump. 60 ml acetate buffer containing 17.4 mg Poly A added via capillary 20 ml lipid solution added via capillary | 10000 | 15 ml/min for acetate buffer with Poly A via syringe pump 5 ml/min for organic lipid phase via peristaltic pump | Dual capillary (20 mm over levitronic pump head) | 5 min after addition: 104.6 101.9 30 min after addition: 97.86 95.91 | 0.207 0.216 0.197 0.200 |

TABLE 8

Example VIII results

| Experiment number | Total lipids concentration in EtOH | Total volume in system [g] | Pump speed [rpm] | Addition rate of organic solution [ml/min] | Capillary type/distance to pump | Zav (backscattering) | PDI |
|---|---|---|---|---|---|---|---|
| 21836/37 | 15 mM (thereof 7.5 mM DODMA) | 150 ml 112.5 ml acetetate buffer pH 4.0 initially as outer phase in levitronic pump. 37.5 ml lipid solution added via capillary | 14000 | 5 ml/min for organic lipid phase via syringe pump | single capillary (20 mm over levitronic pump head) | 5 min after addition: 122.2 115.6 30 min after addition: 135.4 135.0 After adjustment to pH 7: 115.1 112.7 | 0.367 0.340 0.292 0.289 0.258 0.244 |

TABLE 9

Example IX results

| Experiment number | N:P Verhältnis | Total volume in system [g] | Pump speed [rpm] | Addition rate of organic solution [ml/min] | Capillary type/distance to pump | Zav (backscattering) | PDI |
|---|---|---|---|---|---|---|---|
| 21836/38 | 15 | 150 ml 80 ml of RNase-free water as first phase in pump circuit 35 ml of aqueous poly A solution via capillary 35 ml of PEI solution in 20 mM acetate buffer via capillary | 10000 | 5 ml/min for phases via capillary | Dual capillary 20 mm above pump head | 5 min after metered addition: 46.06 47.25 30 min after metered addition: 60.41 58.79 | 0.434 0.403 0.396 0.422 |

TABLE 10

Example X results

| Experiment number | N:P ratio | Total volume in system [g] | Pump speed [rpm] | Addition rate of organic solution [ml/min] | Capillary type/distance to pump | Zav (backscattering) | PDI |
|---|---|---|---|---|---|---|---|
| 21836/39 | 15 | 150 ml 115 ml of aqueous poly A as first phase via circuit 35 ml of PEI solution in 20 mM acetate buffer via capillary | 10000 | 5 ml/min | Single capillary (20 mm above pump head) | 5 min after metered addition: 41.51 43.27 30 min after metered addition: 102.4 59.99 | 0.336 0.318 0.224 0.325 |

TABLE 11

Example XI results

| Experiment number | Organic phase | Vessel/batch size | Capillary | Pump speed [rpm] | Rate of addition [ml/min] | Zav [nm] (backscattering) | PDI |
|---|---|---|---|---|---|---|---|
| E22RDI001175 | 16 ml of 6.2% RESOMER ® RP d 155, 55.8% ethanol, 38.0% DMSO | Plexiglas tank/ 216 ml after addition of org. phase | Fine (1 mm inner diameter) | 3000 | 10 ml/min | 127.83 | 0.209 |

TABLE 12

Example XII results

| Experiment number | Organic phase | Vessel/batch size | Capillary | Pump speed [rpm] | Rate of addition [ml/min] | Zav [nm] (backscattering) | PDI |
|---|---|---|---|---|---|---|---|
| E22RDI001178 | 16 ml of 5.7% RESOMER ® RP d 255, 51.3% ethanol, 43.0% DMSO | Plexiglas tank/ 216 ml after addition of org. phase | Fine (1 mm inner diameter) | 3000 | 10 ml/min | 53.62 | 0.108 |

TABLE 13

Example XIII results

| Experiment number | Organic phase | Vessel/batch size | Capillary | Pump speed [rpm] | Rate of addition [ml/min] | Zav [nm] (backscattering) | PDI |
|---|---|---|---|---|---|---|---|
| E22RDI001182 | 16 ml of 7% RESOMER ® RP d 505, 62.6% ethanol, 30.4% DMSO | Plexiglas tank/ 216 ml after addition of org. phase | Fine (1 mm inner diameter) | 3000 | 10 ml/min | 34.94 | 0.080 |

TABLE 14

Example XIV results

| Experiment number | Organic phase | Vessel/batch size | Capillary | Pump speed [rpm] | DP/CP ration/Rate of addition [ml/min] | Particle size [µm] | Span |
|---|---|---|---|---|---|---|---|
| E21RDI006440 | 5% PLGA in Ethylacetate (7 ml) | Plexiglas tank/ 200 ml after addition of org. phase | Fine (1 mm inner diameter) | 3000 | 1:3/ 2 ml/min (DP) 6 ml/min (CP) | 27.6 | 1.362 |
| E21RDI006441 | 10% PLGA in Ethylacetate (7 ml) | Plexiglas tank/ 200 ml after addition of org. phase | Fine (1 mm inner diameter) | 3000 | 1:3/ 2 ml/min (DP) 6 ml/min (CP) | 39 | 1.363 |
| E21RDI006441 | 20% PLGA in Ethylacetate (7 ml) | Plexiglas tank/ 200 ml after addition of org. phase | Fine (1 mm inner diameter) | 3000 | 1:3/ 2 ml/min (DP) 6 ml/min (CP) | 55.2 | 1.199 |
| E21RDI006442 | 5% PLGA in Ethylacetate (7 ml) | Plexiglas tank/ 200 ml after addition of org. phase | Fine (1 mm inner diameter) | 2000 | 1:3/ 2 ml/min (DP) 6 ml/min (CP) | 38.4 | 1.233 |
| E21RDI006442 | 5% PLGA in Ethylacetate (7 ml) | Plexiglas tank/ 200 ml after addition of org. phase | Fine (1 mm inner diameter) | 4000 | 1:3/ 2 ml/min (DP) 6 ml/min (CP) | 19.9 | 1.634 |
| E21RDI006443 | 10% PLGA in Ethylacetate (7 ml) | Plexiglas tank/ 200 ml after addition of org. phase | Fine (1 mm inner diameter) | 3000 | 1:3/ 1 ml/min (DP) 3 ml/min (CP) | 35.5 | 1.314 |

TABLE 14-continued

Example XIV results

| Experiment number | Organic phase | Vessel/batch size | Capillary | Pump speed [rpm] | DP/CP ration/Rate of addition [ml/min] | Particle size [μm] | Span |
|---|---|---|---|---|---|---|---|
| E21RDI006443 | 10% PLGA in Ethylacetate | Plexiglas tank/ 200 ml after addition of org. phase | Fine (1 mm inner diameter) | 3000 | 1:3/ 4 ml/min (DP) 12 ml/min (CP) | 33.3 | 1.225 |
| E21RDI006443 | 10% PLGA in Ethylacetate | Plexiglas tank/ 200 ml after addition of org. phase | Fine (1 mm inner diameter) | 3000 | 1:3/ 8 ml/min (DP) 24 ml/min (CP) | 34.4 | 1.239 |
| E21RDI006443 | 10% PLGA in Ethylacetate | Plexiglas tank/ 200 ml after addition of org. phase | Fine (1 mm inner diameter) | 3000 | 1:3/ 16 ml/min (DP) 48 ml/min (CP) | 29.4 | 1.561 |
| E21RDI006443 | 10% PLGA in Ethylacetate | Plexiglas tank/ 200 ml after addition of org. phase | Fine (1 mm inner diameter) | 3000 | 1:1/ 8 ml/min (DP) 8 ml/min (CP) | 36.5 | 1.328 |
| E21RDI006443 | 10% PLGA in Ethylacetate | Plexiglas tank/ 200 ml after addition of org. phase | Fine (1 mm inner diameter) | 3000 | 1:5/ 8 ml/min (DP) 40 ml/min (CP) | 31.0 | 1.494 |
| E21RDI006460 | 10% PLGA in Ethylacetate (7 ml) 10% Meloxicam in relation to polymer | Plexiglas tank/ 200 ml after addition of org. phase | Fine (1 mm inner diameter) | 3000 | 1:3/ 8 ml/min (DP) 24 ml/min (CP) | 45.2 | 1.509 |
| E21RDI006465 | 10% PLGA in Ethylacetate (7 ml) 20% Meloxicam in relation to polymer | Plexiglas tank/ 200 ml after addition of org. phase | Fine (1 mm inner diameter) | 3000 | 1:3/ 8 ml/min (DP) 24 ml/min (CP) | 87.6 | 1.199 |

LIST OF REFERENCE NUMERALS

0 Apparatus
1 First reservoir vessel
2 Second reservoir vessel
3 Active element
4 First feed conduit
Second feed conduit
6 Pump
7 Propulsion means
7+ Rotating field
8 Discharge
8+ Circuit
9 Withdrawal fitting
11 Frame
11 Cone
12 First pipeline
13 Ground end
14 Second pipeline
15 Third pipeline
16 Inner wall
17 Housing
18 Rotor
111 Insert
1111 Charging fitting

The invention claimed is:

1. An apparatus for producing nanocarriers and/or nano-formulations, the apparatus comprising:
   a) a first reservoir vessel for accommodating a first liquid phase;
   b) a second reservoir vessel for accommodating a second liquid phase;
   c) an active element for providing an at least biphasic mixture by mixing the first liquid phase with the second liquid phase;
   d) a first feed by which the first reservoir vessel is in fluid communication with the active element;
   d) a second feed by which the second reservoir vessel is in fluid communication with the active element;
   f) a collection vessel for accommodating the mixture;
   g) a discharge by which the active element is in fluid communication with the collection vessel;
   h) a pump which is incorporated in the discharge in such a way that the mixture is conveyable by the pump from the active element via the discharge into the collection vessel;
   wherein
   the first feed and the second feed are vertically oriented at least on a vertical section;
   on the vertical section the second feed is arranged inside the first feed; and
   on the vertical section the first feed or the second feed or both feeds are axially displaceable such that an axial position of the second feed relative to the first feed is adjustable.

2. The apparatus as claimed in claim 1, wherein the first feed inside the vertical section is formed from a first linear pipeline, wherein the second feed inside the vertical section is formed from a second linear pipeline, and wherein the first linear pipeline and the second linear pipeline extend coaxially on the vertical section.

3. The apparatus as claimed in claim 1, further comprising a third reservoir vessel for accommodating a third liquid phase and a third feed by which the third reservoir vessel is in fluid communication with the active element,
   wherein the active element is adapted for providing an at least triphasic mixture by mixing the first liquid phase with the second liquid phase and the third liquid phase, and wherein the first feed inside the vertical section is formed from a first linear pipeline, the second feed inside the vertical section is formed from a second linear pipeline, and the third feed inside the vertical section is formed from a third linear pipeline, wherein
a) the third feed is vertically oriented at least on the vertical section;
b) on the vertical section the third feed is arranged inside the first feed; and
c) the third feed is axially displaceable on the vertical section such that an axial position of the third feed relative to the first feed is adjustable.

4. The apparatus as claimed in claim 3, wherein on the vertical section the third feed is arranged inside the second feed.

5. The apparatus as claimed in claim 1, wherein the pump is in the form of a centrifugal pump which comprises a housing and a rotor which is rotatably mounted in the housing around a rotational axis and is rotatably propellable via a propulsion means.

6. The apparatus as claimed in claim 5, wherein the rotational axis of the rotor is vertically oriented and wherein a horizontal section of the discharge extends in a rotational plane of the rotor.

7. The apparatus as claimed in claim 5, wherein the rotor is magnetically mounted in the housing and wherein the propulsion means is a rotating field which allows mechanically contactless power transmission from the propulsion means to the rotor.

8. The apparatus as claimed in claim 1, wherein the collection vessel and the first reservoir vessel are identical and wherein the discharge is in the form of a circuit.

9. The apparatus as claimed in claim 1, wherein a volume flow of the pump is adjustable.

10. The apparatus as claimed in claim 1, further comprising at least one metered addition apparatus adapted for metered addition of the second liquid phase into the active element.

11. The apparatus as claimed in claim 3, further comprising at least one metered addition apparatus adapted for metered addition of the third liquid phase into the active element.

12. The apparatus as claimed in claim 10, wherein a volume flow of a metered addition apparatus is adjustable.

13. A process for producing a nanocarrier and/or a nanoformulation, the process comprising:
a) providing the apparatus according to claim 1;
b) providing the first liquid phase in the first reservoir vessel, wherein the first liquid phase contains a first liquid dispersion medium;
c) providing the second liquid phase in the second reservoir vessel, wherein the second liquid phase is a second liquid dispersion medium and contains at least one component selected from the group consisting of a precursor to a nanocarrier, a precursor to an active ingredient, and an active ingredient;
d) propelling the pump to establish a liquid flow from the first reservoir vessel via the first feed into the active element and via the discharge into the collection vessel;
e) metering the second liquid phase via the second feed into the active element, wherein a volume flow of the second liquid phase in the second feed is smaller than a volume flow of the liquid flow in the first feed;
f) mixing the first liquid phase and the second liquid phase in the active element to obtain a mixture containing a nanocarrier and/or a nanoformulation;
g) collecting the mixture in the collection vessel;
h) withdrawing the mixture from the apparatus; and
i) optionally, working up the mixture.

14. The process as claimed in claim 13,
wherein the apparatus further comprises a third reservoir vessel for accommodating a third liquid phase and a third feed by which the third reservoir vessel is in fluid communication with the active element,
wherein the active element is adapted for providing an at least triphasic mixture by mixing the first liquid phase with the second liquid phase and the third liquid phase, and wherein the first feed inside the vertical section is formed from a first linear pipeline, the second feed inside the vertical section is formed from a second linear pipeline, and the third feed inside the vertical section is formed from a third linear pipeline,
wherein
the third feed is vertically oriented at least on the vertical section;
on the vertical section the third feed is arranged inside the first feed; and
the third feed is axially displaceable on the vertical section such that an axial position of the third feed relative to the first feed is adjustable;
the process comprising:
a) providing the first liquid phase in the first reservoir vessel, wherein the first liquid phase contains the first liquid dispersion medium and wherein the pH of the first liquid phase is between 6 and 8;
b) providing the second liquid phase in the second reservoir vessel, wherein the second liquid phase contains the second liquid dispersion medium and at least one precursor to a nanocarrier and/or to an active ingredient, and wherein a pH of the second liquid phase is between 3 and 5;
c) providing the third liquid phase in the third reservoir vessel, wherein the third liquid phase comprises a third liquid dispersion medium and at least one further component, wherein the further component is selected from the group consisting of a precursor to a nanocarrier, an active ingredient, and a precursor to an active ingredient;
d) propelling the pump to establish a liquid flow from the first reservoir vessel via the first feed into the active element and via the discharge into the collection vessel; and
e) mixing the first liquid phase and the second liquid phase and the third liquid phase by metering the third liquid phase via the third feed into the active element, wherein a volume flow of the third liquid phase in the third feed is smaller than the volume flow of the liquid flow in the first feed.

15. The process as claimed in claim 13, wherein the first liquid dispersion medium is water and the second liquid dispersion medium is an organic substance.

16. The process as claimed in claim 15, wherein the organic substance is a monohydric or polyhydric alcohol.

17. The process as claimed in claim 16, wherein the precursor to the nanocarrier is a phosphatidylcholine.

18. The process as claimed in claim 15, wherein the first liquid phase contains a buffer.

19. The process as claimed in claim 15, wherein the first liquid phase contains a buffer and wherein the second liquid phase contains the active ingredient or the precursor to the active ingredient.

20. The process as claimed in claim 15, wherein the first liquid phase contains a buffer and wherein the second liquid phase contains two precursors to a nanocarrier.

21. The process as claimed in claim 13, wherein the apparatus further comprises at least one metered addition apparatus adapted for metered addition of the second liquid phase into the active element, and wherein the first liquid phase is circulated before or during the metered addition of the second liquid phase.

22. A process for producing a microcarrier and/or a microformulation, the process, comprising the steps of:
   a) providing the apparatus according to claim 1;
   b) providing the first liquid phase in the first reservoir vessel, wherein the first liquid phase contains a first liquid dispersion medium;
   c) providing the second liquid phase in the second reservoir vessel, wherein the second liquid phase is a second liquid dispersion medium and contains at least one component selected from the group consisting of a precursor to a microcarrier, a precursor to an active ingredient, and an active ingredient;
   d) propelling the pump to establish a liquid flow from the first reservoir vessel via the first feed into the active element and via the discharge into the collection vessel;
   e) metering the second liquid phase via the second feed into the active element, wherein a volume flow of the second liquid phase in the second feed is smaller than a volume flow of the liquid flow in the first feed;
   f) mixing the first liquid phase and the second liquid phase in the active element to obtain a mixture containing a microcarrier and/or a microformulation;
   g) collecting the mixture in the collection vessel;
   h) withdrawing the mixture from the apparatus; and
   i) optionally, working up the mixture.

* * * * *

UNITED STATES PATENT AND TRADEMARK OFFICE
CERTIFICATE OF CORRECTION

PATENT NO. : 11,969,507 B2
APPLICATION NO. : 18/550409
DATED : April 30, 2024
INVENTOR(S) : Gomez et al.

It is certified that error appears in the above-identified patent and that said Letters Patent is hereby corrected as shown below:

On the Title Page

Column 2, Line 2 item (57), in ABSTRACT currently reads:
"and or"
And should read:
--and/or--;

Column 2, Line 4 item (57), in ABSTRACT currently reads:
"to"
And should read:
--to an--; and On page 2, Column 2, Line 5 in OTHER PUBLICATIONS currently reads:
"2022,"
And should read:
--2022, 2023/0138197--.

Signed and Sealed this
Sixteenth Day of July, 2024

Katherine Kelly Vidal
*Director of the United States Patent and Trademark Office*